(12) United States Patent
Hoyt et al.

(10) Patent No.: US 6,403,947 B1
(45) Date of Patent: Jun. 11, 2002

(54) HIGH-EFFICIENCY MULTIPLE PROBE IMAGING SYSTEM

(75) Inventors: Clifford C. Hoyt, Needham; Richard M. Levenson, Brookline; Peter J. Miller, Newburyport, all of MA (US)

(73) Assignee: Cambridge Research & Instrumentation Inc., Boston, MA (US)

( * ) Notice: Subject to any disclaimer, the term of this patent is extended or adjusted under 35 U.S.C. 154(b) by 0 days.

(21) Appl. No.: 09/526,938

(22) Filed: Mar. 16, 2000

Related U.S. Application Data

(60) Provisional application No. 60/125,047, filed on Mar. 18, 1999.

(51) Int. Cl.[7] .............................. G01J 3/50; G01N 21/25
(52) U.S. Cl. ........................................ 250/226; 356/417
(58) Field of Search ........................... 250/226, 208.1, 250/458.1, 459.1, 461.1, 461.2; 356/416, 419, 417

(56) References Cited

U.S. PATENT DOCUMENTS

| | | | |
|---|---|---|---|
| 4,127,773 A | * | 11/1978 | West ........................ 250/461.1 |
| 4,308,456 A | | 12/1981 | Van Der Gaag et al. |
| 4,833,332 A | | 5/1989 | Robertson, Jr. et al. |
| 4,905,169 A | | 2/1990 | Buican et al. |
| 5,029,245 A | | 7/1991 | Keeränen et al. |
| 5,104,512 A | | 4/1992 | Gombocz et al. |
| 5,117,466 A | | 5/1992 | Buican et al. |
| 5,137,364 A | | 8/1992 | McCarthy |
| 5,208,651 A | | 5/1993 | Buican |
| 5,216,484 A | | 6/1993 | Chao et al. |
| 5,223,917 A | * | 6/1993 | Richert ........................ 356/407 |
| 5,306,618 A | | 4/1994 | Praober et al. |
| 5,310,248 A | * | 5/1994 | King et al. ................... 299/1.1 |
| 5,319,435 A | | 6/1994 | Melle et al. |
| 5,377,003 A | | 12/1994 | Lewis et al. |
| 5,410,412 A | | 4/1995 | Gombocz et al. |
| 5,442,438 A | | 8/1995 | Batchelder et al. |
| 5,491,343 A | | 2/1996 | Brooke |
| 5,515,169 A | | 5/1996 | Cargill et al. |
| 5,539,517 A | | 7/1996 | Cabib et al. |
| 5,556,790 A | | 9/1996 | Pettit |
| 5,567,937 A | | 10/1996 | Pinkus |

(List continued on next page.)

OTHER PUBLICATIONS

Technical Note: Digital Image Color Compensation With Unequal Integration Periods, Bioimaging 2 (1994), pp. 160–162; printed in the UK.
Color Compensation For Digitized FISH Images, Bioimaging 1 (1993), pp. 159–165, printed in the UK.
Liquid Crystal Tunable Filter Raman Chemical Imaging, Morris et al., Official Publication of the Society for Applied Spectroscopy, vol. 50, No. 6, 1996, pp. 805–0811.
Liquid Crystal Tunable Filters Boost Fluorescence Imaging, Biophotonics International, Photonic Solutions for Biotechnology and Medicine, Jul./Aug. 1996.

*Primary Examiner*—Stephone Allen
*Assistant Examiner*—Eric Spears
(74) *Attorney, Agent, or Firm*—Cohen, Pontani, Lieberman & Pavane

(57) ABSTRACT

An imaging system is disclosed which provides means for obtaining images with essentially diffraction-limited spatial resolution, and can distinguish between several species of probes within a sample. It may be used with fluorescent, luminescent, up-converting reporter, quantum dot, and other types of probes. Two or more exposures are taken through a filter which expresses different filter states, one of which is preferably a relatively neutral state with high transmission for all wavelengths of interest, and the others of which provide predetermined variation in transmission that are preferably sloping or periodic in wavelength. The probe species is identified by the ratio of response at the various filter settings.

40 Claims, 18 Drawing Sheets

U.S. PATENT DOCUMENTS

| | | |
|---|---|---|
| 5,591,981 A | 1/1997 | Heffelfinger et al. |
| 5,608,213 A | 3/1997 | Pinkus et al. |
| 5,627,648 A | 5/1997 | Garrett |
| 5,703,357 A | 12/1997 | Shih et al. |
| 5,723,294 A | 3/1998 | Glass et al. |
| 5,784,152 A | 7/1998 | Heffelfinger et al. |
| 5,784,162 A | 7/1998 | Cabib et al. |
| 5,817,462 A | 10/1998 | Garini et al. |
| 5,835,214 A | 11/1998 | Cabib et al. |
| 5,863,504 A | 1/1999 | Heffelfinger et al. |
| 6,075,595 A | 6/2000 | Malinen |

* cited by examiner

HIGH-EFFICIENCY MULTIPLE PROBE IMAGING SYSTEM

This application claims benefit of provisional application No. 60/125,047, filed Mar. 18, 1999.

BACKGROUND OF THE INVENTION

1. Field of the Invention

The present invention relates to equipment and methods for imaging a sample which may contain one or more species of luminous probes such as fluorescent probes, luminescent probes, quantum dot probes, up-converting probes, or other emissive probes; and more specifically, to equipment and methods which can image N species of probes with high optical efficiency, often requiring fewer than N observations of the sample.

2. Description of the Related Art

It is often of practical importance to image multiple luminous probes in a single sample, as in fluorescence in-situ hybridization (FISH), in chromatography plate readers, DNA sequencing, spectral karyotyping, general biological and neurobiological research, and the like.

One approach to multiprobe imaging, taken by Glass et. al. in U.S. Pat. No. 5,723,294 is simply to image the sample, in this case a multiwell plate, in several plate readers one after another. By suitable choice of probes and reader settings, unambiguous readings can be obtained from the combined results of all the readers. Yet this is hardly an integrated, efficient solution to the problem.

There is also a large literature of hyperspectral imaging, which can be used to obtain multiprobe images of samples. In hyperspectral imaging, several exposures of a sample are recorded using filters or interferometers in the optical path, from which an optical spectrum is derived for each point in the sample under study. Specific hardware for hyperspectral imaging includes filter wheels and circular-variable filters as in U.S. Pat. No. 5,591,981 and U.S. Pat. No. 5,784,152; angle-tuned interference filters as in the Renishaw imaging Raman microscope described in U.S. Pat. No. 5,442,438; acousto-optical tunable filters (AOTFs) as in U.S. Pat. No. 5,216,484, U.S. Pat. No. 5,377,003, and U.S. Pat. No. 5,556,790; optical interferometers as in U.S. Pat. No. 5,835,214, U.S. Pat. No. 5,817,462, U.S. Pat. No. 5,539,517, and U.S. Pat. No. 5,784,162; and liquid crystal tunable filters (LCTFs) as in Morris, et. al., "Imaging Spectrometers for Fluorescence and Raman Microscopy: Acousto-Optic and Liquid Crystal Tunable Filters," Applied Spectroscopy, 48:7:857–866, 1994. All of these except the interferometer systems are termed band-sequential systems, as each image records the entire spatial content of the sample, and successive images serve to step through its spectral content.

Alternatively, dispersive systems are used to obtain a spectrum for a single point or line, which is then scanned in two or one dimension respectively, to obtain a 2-D image of the sample with spectral data for each point. A non-dispersive system is described by Buican et. al., who use a photoelastic modulator (PEM) and polarizer in U.S. Pat. No. 4,905,169 to determine the spectral contents of a single point via the Fourier analysis of time-series intensity values at a detector; in U.S. Pat. No. 5,117,466 this arrangement is coupled with a laser scanning system to produce a two-dimensional image. Such systems are termed point-sequential or line-sequential imagers, as the entire spectral content is recorded more or less simultaneously, and successive readings step through the spatial content either pointwise or a line at a time.

Prior art describes fluorescence imaging where the excitation and/or emission selection is set to discrete wavelength settings (U.S. Pat. No. 5,784,152), and where the wavelength selection is continuously tunable (U.S. Pat. No. 5,591,981 and U.S. Pat. No. 5,863,504). Excitation light tuning is achieved by filter means such filter wheels, AOTF's, LCTF's; or via galvanometer-driven gratings; or via a series of paddle-mounted filters; or two arc lamps, each of which has control means for rapidly adjusting its intensity over a wide range (U.S. Pat. No. 5,491,343). In U.S. Pat. No. 5,208,651, Buican describes a method for time-encoding the excitation spectrum while concurrently analyzing the emission spectrum, via two PEM elements.

Normally, the individual bands used in hyperspectral imaging are distinct or nearly so, overlapping only in the transition region where a given band cuts off and the adjacent band cuts on. Each band has a transmission vs. wavelength response that approximates a steep-edged trapezoid, with sharp cut-on and cut-off, and approximately constant transmission through the passband. It is a universal goal in hyperspectral imaging to maximize the transmission at all wavelengths in the passband, as this yields increased signal-to-noise, which is a general concern in the field. Researchers have developed methods for broadening the inherently narrow bandpass of the AOTF, to obtain an approximately trapezoidal bandpass instead of a narrow sync function.

The prior art includes other methods for increasing throughput to obtain better signal-to-noise, such as the use of LCTF filters based on Solc designs, with broad bandpasses for increased throughput (Hoyt, "Tunable Liquid Crystal Filters Boost Fluorescence Imaging", BioPhotonics, July/August 1996). This may result in some overlap, or crosstalk, between adjacent spectral bands, which is dealt with by methods such as those described in the next three paragraphs. Notwithstanding the overlap between bands, this art is practiced with trapezoidal bandpass shapes or the like, having the highest practical transmission in each passband.

Many integrated multiprobe readers seek to take advantage of a priori knowledge of the samples being imaged. As the probes have more or less predetermined spectra, a complete spectrum may not be required. For example, it is not necessary to produce spectral data for those wavelength bands at which there is no possibility of optical emission. At the same time, the emission spectra of the various probes involved are not always distinct, but may also overlap to a considerable degree in some cases. If it is not possible to choose a set of wavelengths that correspond in a one-to-one fashion with the probes being imaged, the presence of emission at any given wavelength does not uniquely specify which probe was present. Rather, for a given experimental set-up, the observed energy $e_i$ at wavelength band $\lambda_i$ is related to the concentration of the various probes $c_j$ according to:

$$e_i = a_{i1}*c_1 + a_{i2}*c_2 + a_{i3}*c_3 \ldots a_{iN}*c_N \qquad [1]$$

where coefficient $a_{ij}$ specifies the optical radiation of probe j into wavelength band i.

This provides an easy way to determine the probe concentrations from the observed intensities, as follows. Equation [1] may be written in matrix form:

$$E = A*C \qquad [2]$$

where E is the M×1 vector of observed energies at the M spectral bands, A is the M×N matrix of terms $a_{ij}$, and C is the 1×N vector of probe concentrations. The matrix A has a direct physical interpretation. Each column corresponds to the spectrum of each particular probe, while each row corresponds to the emission of the various probes at a particular wavelength band. While some systems use a number of wavelength bands M greater than the number of probes N, it is common to use M=N, and to seek wavelengths where this matrix is approximately diagonal. Physically this means that for every probe, there is a corresponding wavelength band for which most, though not all, of the optical energy comes from that probe.

Since the number of wavelength bands M equals or exceeds the number of probes N, equation [2] may be inverted uniquely or in a least-squares error fashion to solve for the probe concentrations, viz.:

$$C = A^{-1} * E \quad [3]$$

This allows direct calculation of the probe concentrations from the observed spectra, despite the presence of overlap or cross-talk between the spectral bands. Using this approach, Castleman used 3×3 matrices to produce images of three fluorescent probes from three raw intensity images of sample emission, in "Color Compensation for Digitized FISH images," Bioimaging, 1:159–165, 1993, and again in "Digital Image Color Compensation with Unequal Integration Periods," Bioimaging, 2:160–162, 1994. The raw intensity images were obtained using a color CCD camera. In the BioPhotonics article cited above, Hoyt teaches the use of a fluorescence microscope with a monochrome CCD detector and an LCTF tuned to N bandpass settings in sequence, to image N probes, where N is typically from 3 to 5. Katzir et. al. also recite the benefits of this approach in U.S. Pat. No. 5,834,203.

However, all the foregoing imaging suffer from significant limitations. Imaging spectroscopic methods require complex and rather expensive hardware, and involve taking at least N exposures, using optical elements of relatively low efficiency. Multiple, long exposures are required, which limits throughput and is impractical with probes that photobleach rapidly. Alternatively, Castleman's use of an RGB camera only resolves three probe species, with emission spectra that more or less correspond to the three primary colors.

In other prior art, photometric methods are known for determining the wavelength of a beam of light, using the differential spectral response of two detectors, or of two optical filters, from whose relative response to an optical signal the wavelength is determined. One such example is Van Der Gaag in U.S. Pat. No. 4,308,456, who uses two detectors coupled with optical filters that have more or less opposite spectral shapes, one with transmission that increases with wavelength and one with transmission that decreases. Garrett teaches in U.S. Pat. No. 5,627,648 how to determine wavelength of a beam of light by successive readings using photodiode with no filter, then with a plurality of filters in sequence, each having prescribed transmission vs. wavelength characteristics. Melle in U.S. Pat. No. 5,319,435, teaches the use of a Bragg-reflector element to create a controlled reflection vs. wavelength response, which is then combined with two photodetectors to provide a wavelength measurement system. Shih et. al. describe a system in U.S. Pat. No. 5,703,357 where light passes through a linear-variable filter onto two detectors having varying aperture ratio along the dispersion axis of the filter. The wavelength of light determines where along the linear variable filter the light passes through to the detectors, and thus determines the aperture ratio between the two detectors. From the ratio of relative response at the two detectors, the system determines the wavelength of incident light.

Gombocz et. al. describe a gel electrophoresis system in U.S. Pat. No. 5,410,412 and U.S. Pat. No. 5,104,512 which uses two photodetectors to view a gel electrophoresis plate, fed by separate fiber optics probes. Interposed in front of the two photodetectors are two filters, one that absorbs over the range 400–600 nm and one that absorbs over the range 500–700 nm. Using the relative response of the two filter-detector combinations and an unspecified Fourier analysis algorithm, the wavelength of light emitted by the gel plate is inferred; the purpose of Fourier methods is unclear. In U.S. Pat. No. 5,515,169, Cargill et. al. provide a wavelength-sensitive instrument similar to that of Gombocz except that the two optical fibers and two filters are replaced with a single beamsplitter that divides incident energy into two beams whose proportion varies linearly with wavelength. The resultant beams are sensed by two photodetectors, and the emission wavelength is determined from the ratio of detector signals via an unspecified algorithm.

Prober teaches in U.S. Pat. No. 5,306,618 a DNA sequencing instrument based on a two-channel photometer, where readings in the two channels indicate strength of sample emission in adjacent wavelength bands, each of which has a trapezoidal bandpass. This system is realized using two photodiodes or photomultiplier tubes, sensing the transmitted and reflected signals from a dichroic interference filter placed in the emission beam, which yields adjacent, complementary bands. Alternatively, Prober teaches dividing the sample emission into two beams, with a suitable bandpass filter and detector in each beam, to achieve the same result. The system is said to distinguish between four fluorescent probes having overlapping emission spectra. The degree of overlap is so great, and the photometer bands are so chosen, that at least three of the four probes, and possibly all four, have significant emission in each photometer band. From the sum of, and the ratio of, signal levels in the two bands, the presence of a probe and its species are determined. However, this system has several weaknesses. First, since the photometer bands are inherently much narrower than the emission spectrum of any given probe, only a small portion of the radiant energy from the sample is actually sensed. This leads to reduced optical sensitivity. Second, it is exquisitely sensitive to shifts in the wavelength of emission by the probes, as a shift of one-eighth of the emission width could lead to misidentification of which species was involved. Shifts of such magnitude can occur in multiprobe experiments, depending upon the chemical properties of the probe, the sample environment, quenching, pH, concentration, and the like. Yet there is no way to use this photometer with more widely-spaced probes, as it relies on the overlap of at least N−1 of the N species within each of the two photometer bands.

These photometric wavelength-detection systems are inherently non-imaging, in that they provide a wavelength indication for the whole beam of light, and cannot determine the wavelength at a plurality of separate points within an image. For gel chromatography or flow cytometry, this may be acceptable since the instrument insures that the material being sampled moves past the single point sensed by the photometer. However, in the vast majority of bio-medical applications, this is a severe limitation. Even in gel chromatography, this results in poor utilization of equipment. The plate reader is occupied for the entire duration of the gel separation, which can take hours; the alternative of a lengthy separation using an inexpensive instrument, followed by a rapid readout cycle in the more costly reader, is impossible.

Gombocz indicates that one can use mechanical means to scan the photometer to sense different regions across the surface of a gel plate. The same is true for the systems of Cargill, Var der Gaag, Buican, or Prober, in that these point-sensing photometric devices could be coupled with a 2-D scanner to provide an image of the sample. However, for this purpose there is little reason to choose these systems over alternatives such as e.g. a fiber-coupled diode-array spectrometer, which would provide more reliable spectral information with better utilization of the scarce emitted photons. The additional complexity of the scanner typically cancels out any innate simplification in the photometric wavemeter component. In short, when coupled to a scanner, the result is a low-performance hyperspectral imaging system, with no clear benefits over the prior art in that realm.

Nor do any prior-art wavelength-measuring systems provide means for directly producing a two-dimensional image with a two-dimensional sensor. Those which involve Fourier methods to determine wavelength are probably ill-suited to a taking a high-definition image, due to the computation requirements when the number of pixels is large. Buican, for example, describes in U.S. Pat. No. 4,905,169, the use of a phalanx of thirty-two computers, in parallel, to handle the data-processing requirements when his approach is used with single-element detectors at moderate data rates (150 $\mu$s per sample reading).

These additional concerns relate to the special properties of imaging systems, which are not addressed by the prior art photometric systems. For example, all the photometric systems utilize ratios between two different measurements of a scene, via two detectors and a beamsplitter and perhaps additional filter elements; or via a single detector with various filters in time-sequence. Systems using two detectors face a significant cost burden over one-detector systems, as the cost of a two-dimensional imaging sensor such as a CCD is high. Either a one- or a two-detector system must provide means for spatially registering the images produced by the two detectors, or produced under various filter settings.

Indeed, this latter requirement is especially stringent since the heart of a photometric wavelength determination is a high-accuracy ratio of the two signal levels. Any error in the spatial registration of the multiple exposures degrades the numerical accuracy of the ratio scheme involved, since if readings from the two detectors come from different spatial regions in the sample, there is no way to take their ratio and determine a wavelength. In contrast, simple color imaging is relatively tolerant of minor mis-registration: the eye is very sensitive to fine spatial detail in the green band, but less so in the red and blue bands. Multi-detector color cameras need not achieve perfect registration between detector bands, yet can still produce an acceptable image. This is not true for an imaging system which yields a ratio-based photometric determination of wavelength, which must be registered to much better than one pixel.

Spatial registration of two detectors to a fraction of one pixel is a challenging and expensive proposition. Similarly, all known prior-art systems that use interference filters employ mechanical means to select between filters, or to engage them into and out of the beam. This mechanical switching leads to image shift from the unavoidable wedge in the filter elements, which corrupts the ratio used to derive a wavelength measurement.

Other practical considerations confound the extension of existing point-measuring photometric systems into imaging systems. The Prober photometer exhibits poor optical efficiency, since only a small portion of the sample emission is utilized by any given photometer band, even the most responsive band. This deficiency is even more problematic in an imaging system, where the desire for high spatial resolution favors the use of imaging detectors with many pixels; this in turn means that the radiant energy is partitioned between a great number of pixels, which exacerbates the signal-to-noise requirements.

In U.S. Pat. No. 4,833,332, Robertson Jr. teaches an improvement to the Prober photometer which is preferably constructed without any lenses or imaging optics, and uses non-imaging detectors such as photomultiplier tubes as detectors. Field-of-view restricting elements such as fiberoptic couplers maintain the desired passband of the filter elements. This arrangement is not capable of imaging a two-dimensional scene.

In another example, Buican's system uses PEM elements to time-encode the spectral content of the beam, and the intensity of the encoded beam is read by a photodetector. Simply replacing the photodiode or photomultiplier tube (PMT) of Buican with a two-dimensional imaging detector such as a CCD, is impractical if not absolutely impossible. To do so would require continuously reading out the image from the CCD synchronously with the modulation by the PEM, which operate at frequencies in excess of 10,000 Hz (typically 50,000 Hz). On the other hand, CCD cameras capable of high-resolution imaging typically have sustained readout rates of 5 to 30 Hz, and even the most specialized high-speed digital cameras do not exceed 1,000 Hz.

In summary, the aforementioned art provides equipment and methods for hyperspectral imaging to produce high-definition images of multiple probes in a sample, but these require at least N observations to resolve N probes and use relatively expensive, optically inefficient hardware. Other systems provide wavelength measurements using photometric means, and require fewer observations or simultaneous observation with two detectors. However, these are point-measuring systems that cannot provide an image of the sample unless one adds mechanical or optical scanning means, which undermines the cost and performance benefits of this approach. And, attempts to extend this art to construct systems with two-dimensional imaging sensors are impractical for at least one of the following reasons in every case: the need for multiple imaging detectors; the need to register multiple images obtained from different detectors, or from a single detector with multiple filters, to much better than a single pixel; poor optical efficiency; the need for mechanical moving parts; intensive computing requirements; or, the need to operate at sample rates far above the capability of imaging detectors.

SUMMARY OF THE INVENTION

The first object of the present invention is to provide a system with high optical efficiency to achieve good signal-to-noise in detecting and discriminating between probes. A second object is to provide for imaging an entire two-dimensional scene at once, with an enormous advantage in throughput compared against the point-detectors or line-imaging systems of the prior art. It is a further object to provide means and methods for high-definition imaging of samples that may contain up to N species of luminous probes, in many cases using fewer than N observations. Yet another goal is to achieve these aims without any moving parts, to eliminate vibration and enhance reliability.

The invention uses filter elements, preferably liquid crystal type, to provide a few filter states, none of which have the conventional bandpass shapes as used in band-sequential multispectral imaging. One state may be an all-pass filter state, in which light of all wavelengths of interest is transmitted essentially without loss from the sample to the detector. A second state imposes a known spectral filter such as a downward- or upward-sloping response across the spectral band of interest. From the relative response of the detector to these two exposures, the wavelength of emission light, and hence the emitting probe species, is determined. While only two exposures are required, the system can distinguish between more than two species, with the resolution limit being set by the available probes and the signal-to-noise of the overall system.

A third exposure may be taken in a third filter state, which has a wavelength response that is linearly independent of the first two states, such as a triangle wave, a non-linear ramp, or a high-order sinusoid. Mathematically, this state is linearly independent from the first two states. Adding this exposure allows resolution of very densely-spaced probes, or enables unambiguous determination of probe species and proportions when a given pixel contains a mixture of two probes.

A key benefit is that in many instances fewer than N exposures are required in order to resolve N species. A second benefit is the high efficiency of the system. One of the filter states can be essentially a clear state, with transmission in excess of 80% if desired. The other filter states can have equally high peak transmissions, with transmission at other wavelengths depending on the filter state (ramp, triangle shape, and so on).

Another benefit is that the cost and complexity of the system are greatly reduced relative to prior-art LCTFs, AOTFs, or interferometers. While it is possible to construct the present invention using an interferometer as the filter element, in preferred embodiments the filter may consist of one or two filter stages as described in U.S. Pat. No. 5,892,612, "Tunable Optical Filter with White State". Or, simple liquid crystal variable retarders between polarizers may employed instead. Generally, only one or two liquid crystal elements are required for the present invention, in contrast with prior-art LCTFs for multispectral imaging, which require from 5 to 12 elements. This reduces construction costs, and since the resulting assembly is typically only 3–6 mm thick, it is readily incorporated into microscopes, macroscopic imaging systems, and cameras without relay optics.

The use of liquid crystal elements as filters has several benefits. Unlike mechanically-scanned interferometric systems, there are no moving parts or precision optical surfaces, nor is the present invention sensitive to ordinary thermal drift. Unlike AOTF systems, no radio-frequency (RF) signals are required, and a large aperture is easily achieved. As with all LCTF imaging systems, diffraction-limited images may be readily obtained. This is a benefit in applications such as FISH, genetic therapy, functional imaging, chromosomal imaging, histological imaging, and the like.

Alternatively, one may use a filter wheel which is populated with filters made using colored glass, colored plastic, dielectric type filters, gels, and combinations of these. In a preferred embodiment of this type, one filter position is empty to provide a substantially clear state. Another filter provides a non-bandpass filter response such as a ramp or a periodic function of wavelength. It is easy to use software post-processing to spatially register images taken through each of the other filters relative to the clear state, as whatever features are present in a given filtered image must also be present in the unfiltered image, which transmits light from all probes. This eliminates the need for multiply-labeling certain species to produce a fiducial signal for registration purposes, as is required in the prior art. Even if no clear state is used, the fact that the filters have slope-type response functions, rather than bandpass-type functions, insures that several probes will be visible through any given filter, and vice versa. So again spatial registration is not a problem, and the prior-art limitation of needing a multiply-labeled fiducial is overcome.

Independent of the type of filter used, a further benefit is that the system obtains highly accurate data without requiring a high degree of uniformity in the imaging sensor employed. Also, the system can normally be used in a self-calibrating fashion, where the properties of the probes and filters are characterized in-situ and variations in chemistry are readily accommodated. Yet another benefit is that the system does not have burdensome computation requirements.

The present invention can be practiced in concert with a variety of imaging equipment, including confocal microscopes, epi- and darkfield illuminated microscopes, plate readers, high-throughput drug screening equipment, and other macroscopic imaging equipment. Acquisition at video rates is practical, which is a boon for high-throughput applications, or for the visualization of multiple probes in real-time.

It is possible to construct the present invention with cameras that have multiple-detectors, each of which views a distinct spectral band and makes species determinations for species emitting in that band, based on ratios of intensity in the various filter settings. This allows imaging plural colocalized probes in a very light-efficient manner. No extraordinary registration of one imaging detector to another is required, since the ratio used for the photometric determination of species is the ratio of two readings from a given detector, rather than one detector compared to another. This embodiment can be practiced with conventional three-CCD RGB cameras as well as custom designs to access other spectral bands.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference numerals denote similar elements throughout the several views.

DETAILED DESCRIPTION OF THE PRESENTLY PREFERRED EMBODIMENTS

In this detailed description of the present inventive imaging system, certain terms are synonymous in meaning and interchangeably used. The terms emission and luminous emission are both used to indicate optical emissions, whether in the visible, ultraviolet (UV), or infrared (IR), from a probe. The terms waveplate and retarder are used equally, to describe an optical waveplate with a specific retardance value. Half-wave plate denotes a waveplate with a retardance of $\lambda/2$ at a specified wavelength $\lambda$, or for wavelengths generally within a wavelength range $[\lambda_1, \lambda_2]$.

The term 'probe' is used to mean any chemical element, compound, or composition which emits light by any mechanism, including without limitation fluorescence, luminescence, electro-luminescence, radioluminescence, bioluminescence, phosphorescence, chemiluminescence, photoluminescence, two-photon processes, up-converting reporters, or photon-phonon processes such as Raman scattering. It explicitly includes living and inert structures of matter such as quantum dot structures, or bioluminescent materials and systems.

Figure 1A:
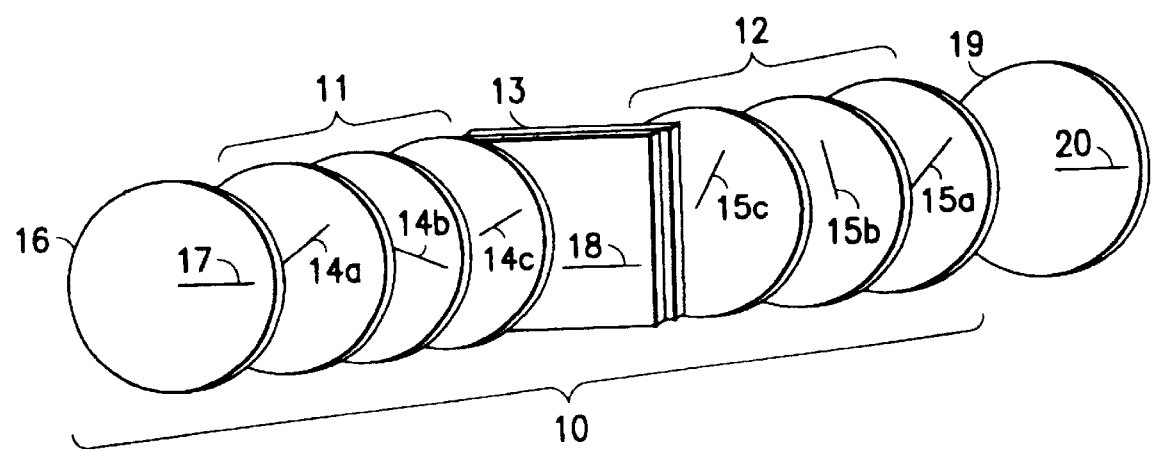
FIG. 1a shows the optical design of a two-state liquid crystal tunable filter (LCTF)

FIG. 1a shows an LCTF constructed according to the U.S. Pat. No. 5,892,612, "Tunable Optical Filter With White State", Miller et. al., the contents of which are hereby made a part of this teaching. In particular it has a symmetric arrangement of retarder networks 11 and 12 located on either side of a liquid crystal cell. Liquid crystal cell 13 is a variable retardance cell with low retardance in a first, electrically-driven state; and a half-wave retardance at $\lambda_{cell}$ in a second state; its slow axis 18 is oriented at 0°. Entrance and exit polarizers 16 and 19 have their transmission axes 17 and 20 oriented at 0°.

Retarders 14a through 14c in network 11 have their slow axes oriented at angles $\{\theta_a, \theta_b, \theta_c\}$ and may have any desired values of retardance R, consistent with obtaining the desired filter response. Elements 15a–15c must meet the symmetry criteria:

$$R_{15a}=R_{14a};\ \theta_{15a}=90°-\theta_{14a} \quad [4a]$$

$$R_{15b}=R_{14b};\ \theta_{15b}=90°-\theta_{14b} \quad [4b]$$

$$R_{15c}=R_{14c};\ \theta_{15c}=90°-\theta_{14c} \quad [4c]$$

While FIG. 1 and equations [4a]–[4c] indicate the use of three retarders per network, the actual number will vary with the design and the desired filter response as taught in Miller et. al., but will always be one or more.

The filter switches between an optically neutral, clear state when the cell 13 is in the half-wave state; and an optical filtering state with transmission properties that are determined by the retarder networks 11 and 12, when cell 13 is in the low-retardance state. The switching is electro-optical, with no moving parts, and transition between the two states occurs in a few milliseconds or less. There is no image shift associated with switching between states, and diffraction-limited images are readily achieved through the use of sufficiently flat optical elements. Methods for designing suitable retarder networks are taught in Miller et. al., along with other classes of network symmetries and other switches for making filters that switch between an optically neutral, clear state and a desired optical filtering state. These alternatives would also be suitable for use in the present Invention.

Figure 1B:
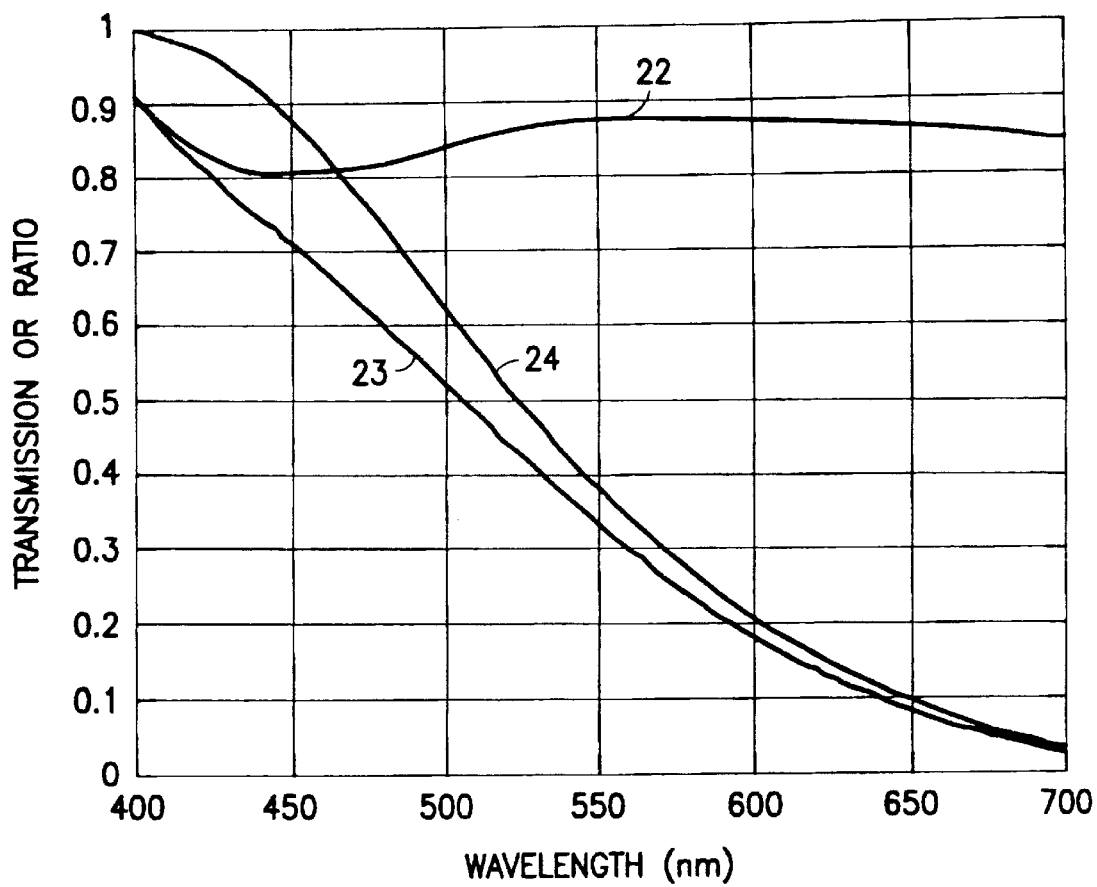
FIG. 1b shows the optical transmission T of the LCTF in each state, and the ratio of the two transmissions.

FIG. 1b shows the transmission of such a switch, where network 11 is comprised of a single retarder 14a of stretched polyvinyl alcohol (PVA) film with 195 nm of optical retardance R, as measured at 633 nm, with its slow axis oriented at $\theta_{14a}=45°$. As per equations [4a]–[4c], retarder network 12 must be a single element of like retardance and material, with its slow axis oriented at $\theta_{15a}=90°-\theta_{14a}=45°$. Liquid crystal cell 13 is a variable-retarder liquid crystal cell, using a 4 micron layer of Merck material MLC-6648 (EM Industries, Hawthorne N.Y.) material sandwiched between substrates of Corning 7059 (Corning, N.Y.) glass onto which indium-in oxide (ITO) electrodes were deposited by Donnelly Applied Fihns (Boulder, Colo.) to a sheet resistivity of 500 Ω/square. Alignment is by means of spin-coated polyimide layers on the substrates which were buffed in an antiparallel geometry, as is known in the art, to orient the liquid crystal director at 0°. Polarizers are Polatechno (Tokyo, Japan) type 18043P material with their transmission axes at 0°.

When no voltage is applied to liquid crystal cell 13, it exhibits an optical retardance R of $\lambda/2$ at 560 nm, and the transmission of the overall assembly 10 for horizontally polarized incident light is given by curve 22 in FIG. 1b, termed $T_1$. When a square-wave signal of 18 Volts RMS is applied to cell 13, it exhibits a very low retardance (15 nm or less), and the transmission of the overall assembly 10 for horizontally polarized light is given by curve 23 in FIG. 1b, termed $T_2$. The filter exhibits essentially no transmission for vertically polarized light in either case. The ratio of transmission $T_2/T_1$ is given by curve 24.

Figure 2:
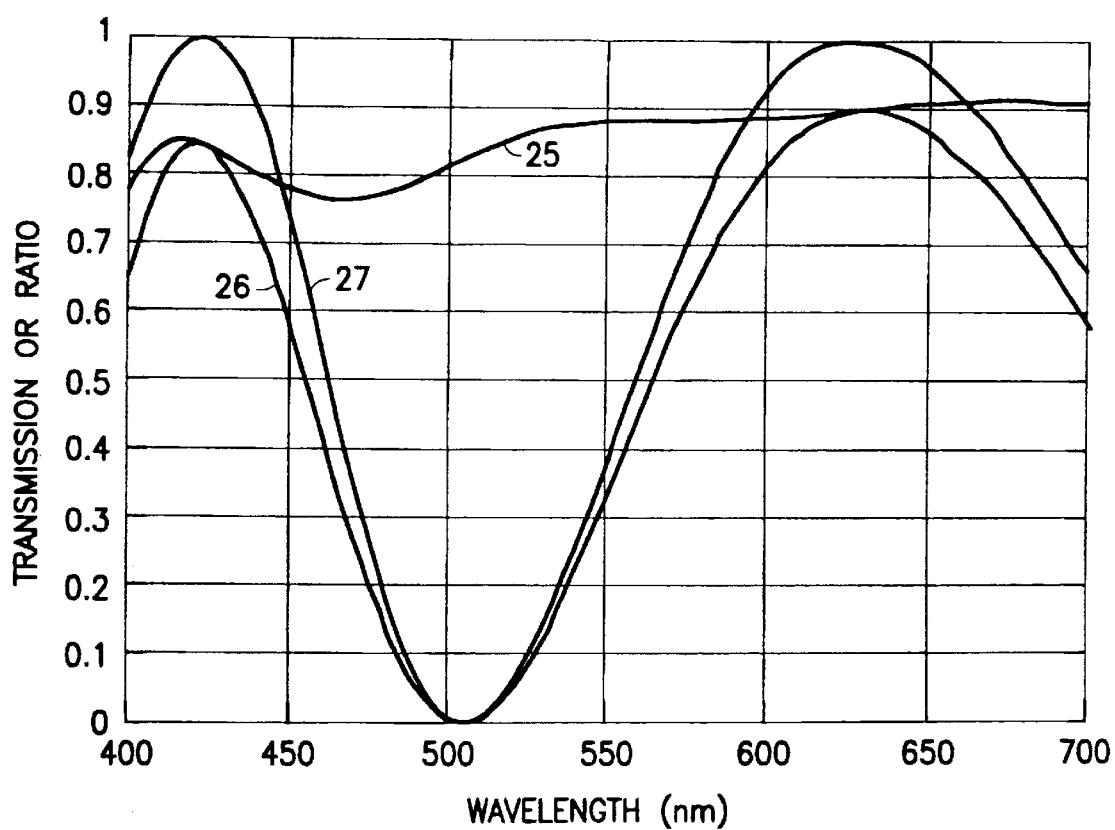
FIG. 2 shows the optical transmission T of a second LCTF in its two states, built with different component values, and the ratio of the two transmissions.

The optical properties of a second filter are shown in FIG. 2. The retarder network 11 is again a single stretched PVA element with its slow axis $\theta_{14a}$ at 45°, although its retardance R is now exactly 1 wave at 627 nm. Liquid crystal cell 13 is identical to that in the previous example, except that it uses material MLC-6816 and exhibits a retardance of $\lambda/2$ at 505 nm when no voltage is applied to it. The same polarizers were used. The transmission of the assembly for polarized light is given by curve 25 as $T_1$ when no voltage is applied to the cell, and by curve 26 as $T_2$ when a square-wave signal of 18 Volts RMS is applied. The ratio $T_2/T_1$ is shown by curve 27.

As illustrated in FIGS. 1b and 2, the arrangement provides for a high-efficiency clear state, with transmission in excess of 80% for polarized light across most of the visible range. The other state is an optically filtering state, which in FIG. 1b is a monotonically decreasing function of wavelength, and in FIG. 2 is a periodic function with two broad peaks and one minimum across the visible band. The ratio of transmissions $T_2/T_1$ has a similar shape to that of $T_2$, since the divisor has a high and nearly constant value throughout the spectral range of interest.

The filter whose transmission is illustrated in FIG. 1b is suitable for practicing the present invention when one seeks to image various probe species that emit at a range of wavelengths spanning the full visible band. The filter illustrated in FIG. 2 would be suitable for imaging probes whose emission spectra are more densely spaced, and span only a portion of the visible over which the filter ratio is monotonic with wavelength, such as 505 nm–630 nm, or 430 nm–500 nm.

However, it is not necessary that the filter response be monotonic with wavelength, either increasing or decreasing; it is sufficient that the filter ratio $T_2/T_1$ be different for each of the probe species involved. So, the filter of FIG. 2 could be used to discriminate between probes emitting at 420 nm, 490 nm, 550 nm, and 670 nm, at which wavelengths the ratio $T_2/T_1$ is 0.98, 0.05, 0.40, and 0.80.

In general, the present Invention discriminates between probe species by the ratio of responses between two or more states. The ratio of overall system responses $E_i/E_j$ does not depend on the absolute responsivity of the detector, nor of the optics used to collect the light, nor of the excitation beam intensity, nor of the brightness of the probe, nor on the degree of focus attained in imaging the probe. It depends solely on the wavelength of light which is being emitted, and the filter responses $T_n$. The other factors act to brighten or weaken the strength of response equally in all filter states. Thus, measurement accuracy is not affected by factors that affect the overall response function $S(\lambda)$ of the system by a scalar, or by variations in the response $S(\lambda)$ between different pixels in an imaging detector.

To produce an image of the various probe species from the raw exposures taken in the various filter states, the first step is to correct for background dark-count levels, and then to take the ratio of responses $E_i/E_j$ in the filter states. Often, only two states are used, in which case a single ratio is obtained. If the ratio falls in the numerical range which is characteristic of a certain probe, it is determined to be that probe. The case where a given pixel or point in an image may contain several probe species is more complex. Methods for identifying when this has occurred, and determining the species involved, are presented in a later portion of this specification.

In many cases, the probe species being sought will be determined in advance, along with the target ratios of response $E_n/E_1$ used to identify probe species. In other cases, it will be desirable to determine the exact target ratios $E_n/E_1$ by direct measurements of samples. This may be done using control samples of known species, or it may be done using ordinary samples, together with approximate estimated values of the target ratios. In this case, the estimates are adjusted in light of the actual data, to yield more reliable data for identification. Provided that the sample expresses all probe species, the values are then updated for all probes. This is done by methods such as plotting histograms of the ratios $T_j/T_i$ among the population of all pixels, for all pixels having a signal in at least one filter setting that exceeds some minimum value. In the overall population, there will be sub-populations corresponding to the various species, which are then identified by correspondence with predetermined targets or the like. The target ratios are then updated in light of the histogram data, and may even be used to identify the species in the sample just analyzed. Thus the method can be used in a self-referencing fashion, to learn and compensate for effects such as shifts in the probe concentration, pH, and the like, which systematically alter the emission wavelength by a small amount.

Figure 3:
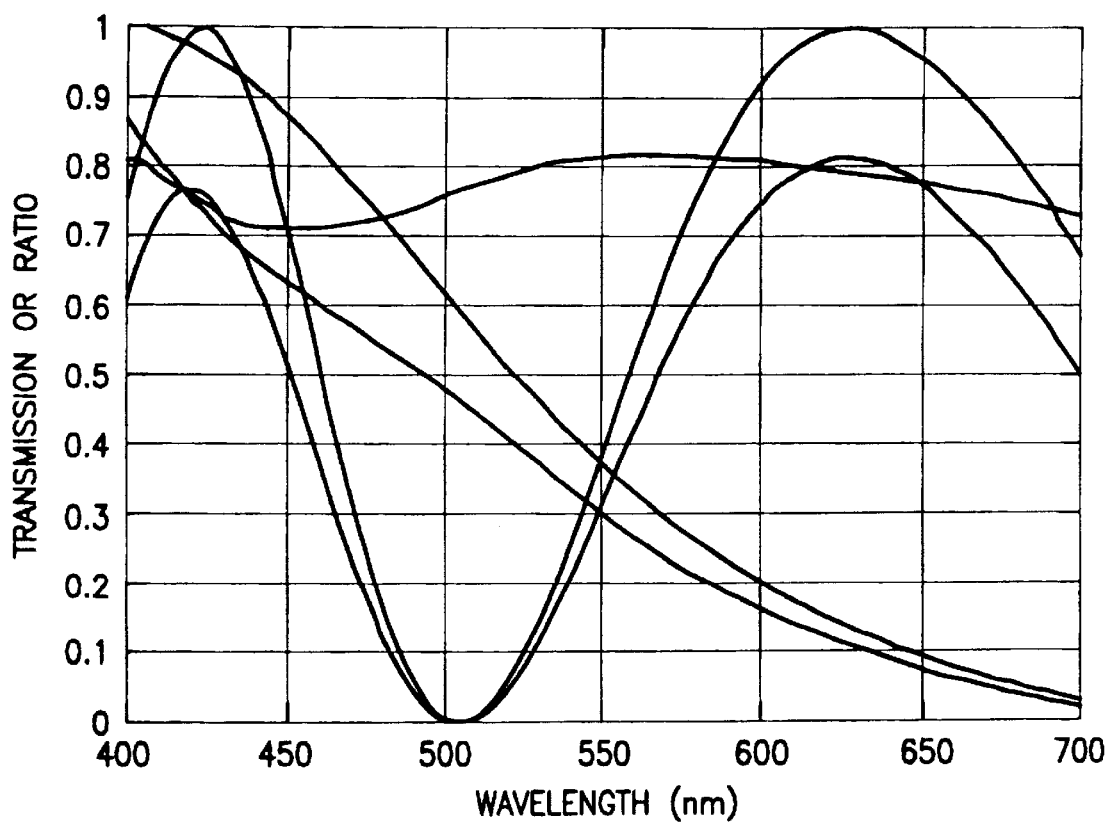
FIG. 3 shows the optical transmission T of an assembly constructed of two LCTFs, built according to FIG. 1 and FIG. 2, placed in optical series, and the ratio of transmissions.

FIG. 3 shows a filter with three states, including a first state $T_1$ with relatively high transmission at all wavelengths, indicated as 31; a second state $T_2$ with monotonically decreasing response indicated as 32; and a third state $T_3$ with periodic response indicated as 34. This arrangement is produced by placing the filter which produced FIG. 1b, in optical series with the filter that produced FIG. 2. When no voltage is applied to either liquid crystal cell, the transmission $T_1$ is obtained; when the first or second element is energized while the other is undriven, the transmissions $T_2$ or $T_3$ is produced. Ratios $T_2/T_1$ and $T_3/T_1$ are shown as curves 33 and 35, respectively.

Such an arrangement is useful in imaging a great many probes, or when adjacent probe species emit over a close wavelength spacing, for which the ratio $T_2/T_1$ is very similar. In this case it is difficult to make an unambiguous determination of species, because factors such as noise in the detector and electronics might lead to a slight error in the observed ratio, and hence a mis-identification. However, over most of its range the ratio $T_3/T_1$ changes much more rapidly with wavelength than the ratio $T_2/T_1$, making it a more sensitive discriminator of adjacent species. On the other hand, there are several widely-spaced wavelengths which have identical ratios $T_3/T_1$, such as 470 nm and 540 nm, between which that measure alone cannot distinguish. So, the ratio $T_2/T_1$ may be used as a coarse determination of wavelength, which eliminates any ambiguity between widely-spaced bands; and the ratio $T_3/T_1$ used for a fine determination, for high sensitivity to distinguish between closely-spaced species.

Figure 4:
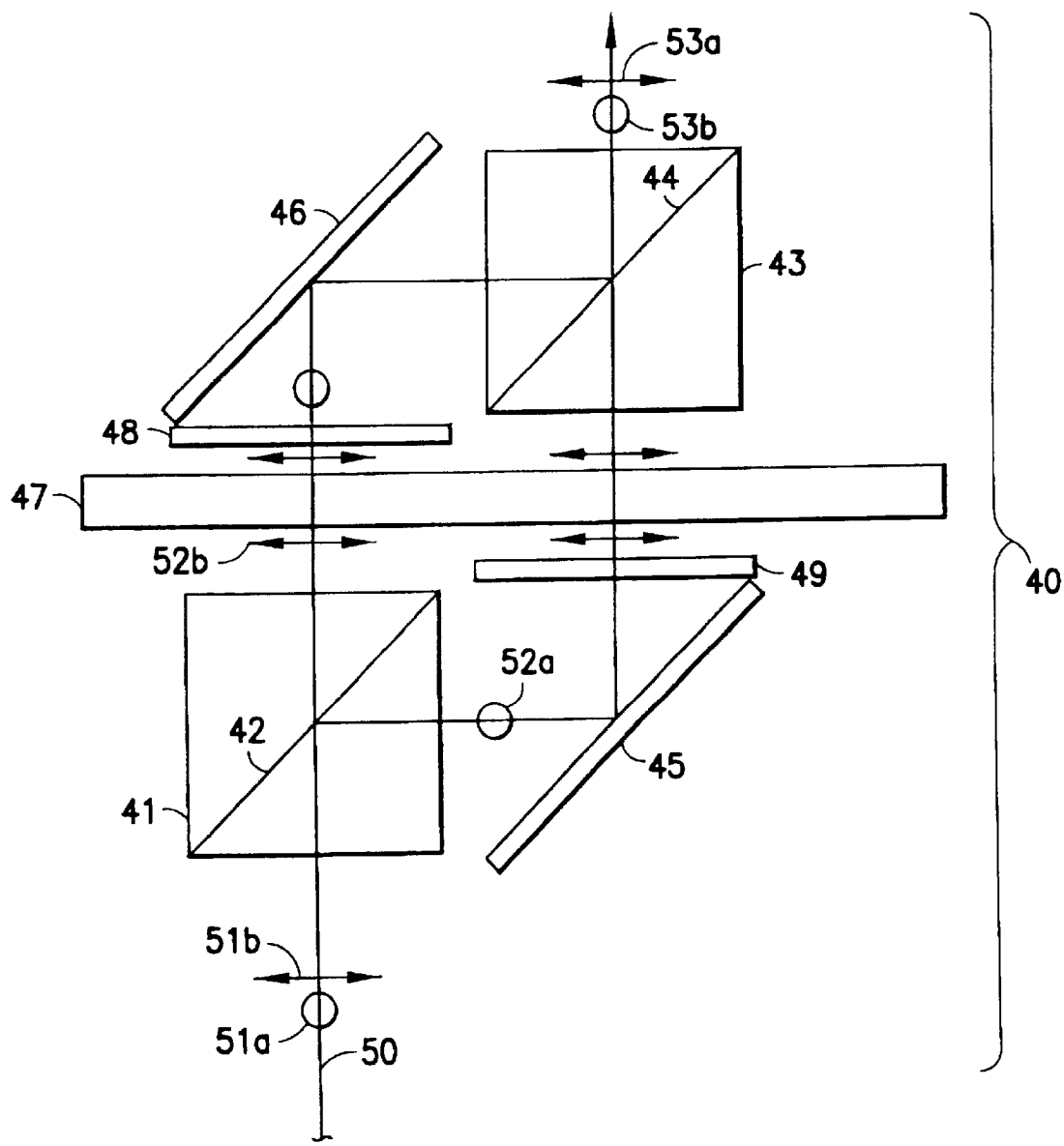
FIG. 4 shows a high-efficiency filter which incorporates a pair of polarizing beamsplitters and mirrors with an LCTF element so as to utilize both polarization states in the incident beam.

FIG. 4 shows a high-efficiency filter 40 comprising an element 47 which transmits only one polarization state of light, where the overall assembly is rendered transmissive to both states of light for higher optical throughput. Incoming beam 50 has components with both linear polarization states 51a and 51b present. These impinge on a polarizing beamsplitter 41, and at its hypotenuse 42 one component 52a is reflected and the other 52b is transmitted. While these are drawn as the S and P components, respectively, the arrangement would work equally well if a polarizing beamsplitter with the complementary relationship were devised and employed as element 41. The transmitted component 52b passes through element 47 and encounters a polarization-sensitive optic 48 which transforms it to the complementary polarization state. It then reflects off of mirror 46 and is reflected at the hypotenuse 44 of a second polarizing beam splitter 43, and emerges as component 53b of the exiting beam. The corresponding reflected component 52a reflects off of mirror 45 and is transformed by polarization-sensitive element 49 into the complementary polarization state. Thus, it enters element 47 in the same state as the other beam. Upon exiting element 47, it passes through polarizing beamsplitter 43 and emerges the system as component 53a of the exiting beam. The overall effect is that by addition of a pair of polarizing beamsplitters, mirrors, and polarizing optics to an LCTF element, one is able to utilize both polarization states in the incident beam.

Suitable polarization optics for use as elements 48 and 49 include without limitation, half-wave plates, polarization rotators with 90° rotation, and twisted-nematic cells. Any device which has the effect of transforming the polarization to the complementary state may be used. Alternatively, the two spatially distinct regions of element 47 through which the two components pass can be constructed to receive, and to transmit, complementary polarization states from one another. This can be achieved by e.g. orienting the polarizing films in complementary fashion in the two regions involved. This eliminates the need for elements 48 and 49. Such variations as just described, and others, will be evident to one skilled in the art of optical systems for polarized light.

The effect of the arrangement in FIG. 4 is a near-doubling of the optical efficiency of the system for unpolarized incident light when used with liquid crystal tunable filters 47. This also allows one to practice this Invention in concert with other imaging modalities such as fluorescence polarization, for which both polarization states must be presented to the detector. However, arrangement 40 is not essential to this Invention, and in cases where there is no need to view both polarization states, and there is sufficient detector response to the sample emission, element 47 may be used on its own with the benefits of economy and reduced size.

Figure 5A:
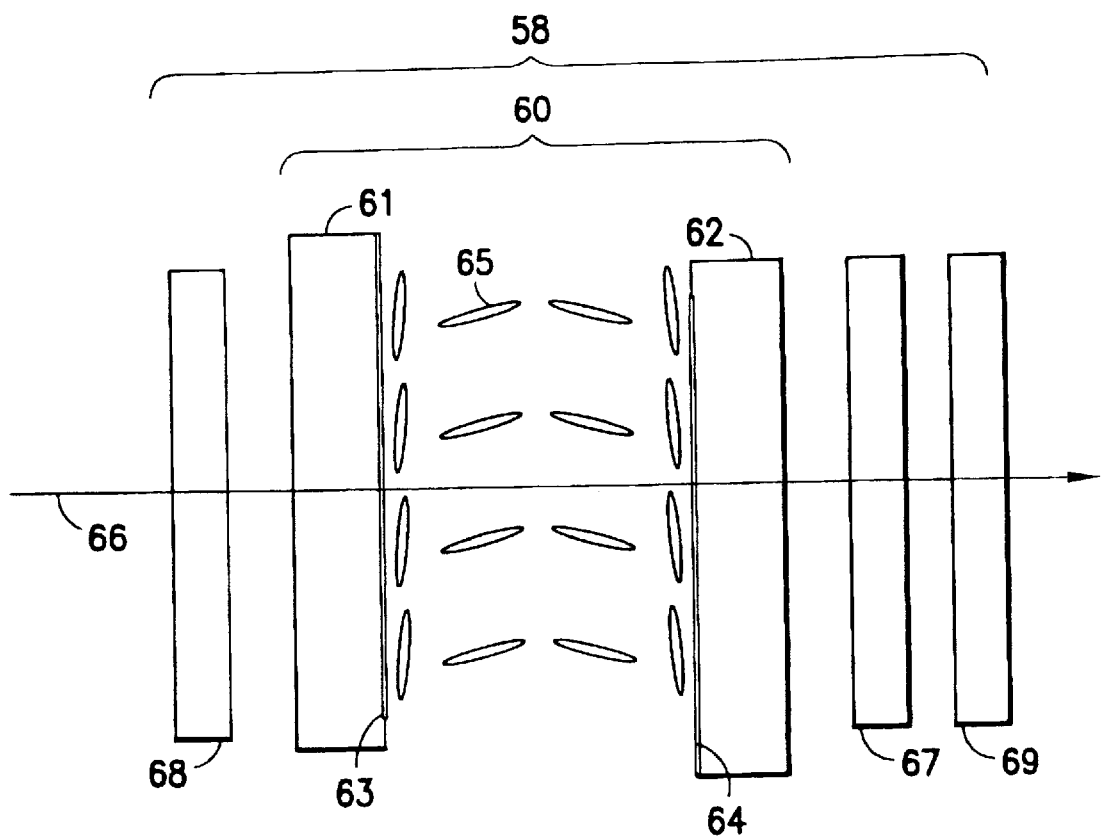
FIG. 5a shows an LCTF consisting of a liquid crystal variable-retardance cell with compensator.
Figure 5B:
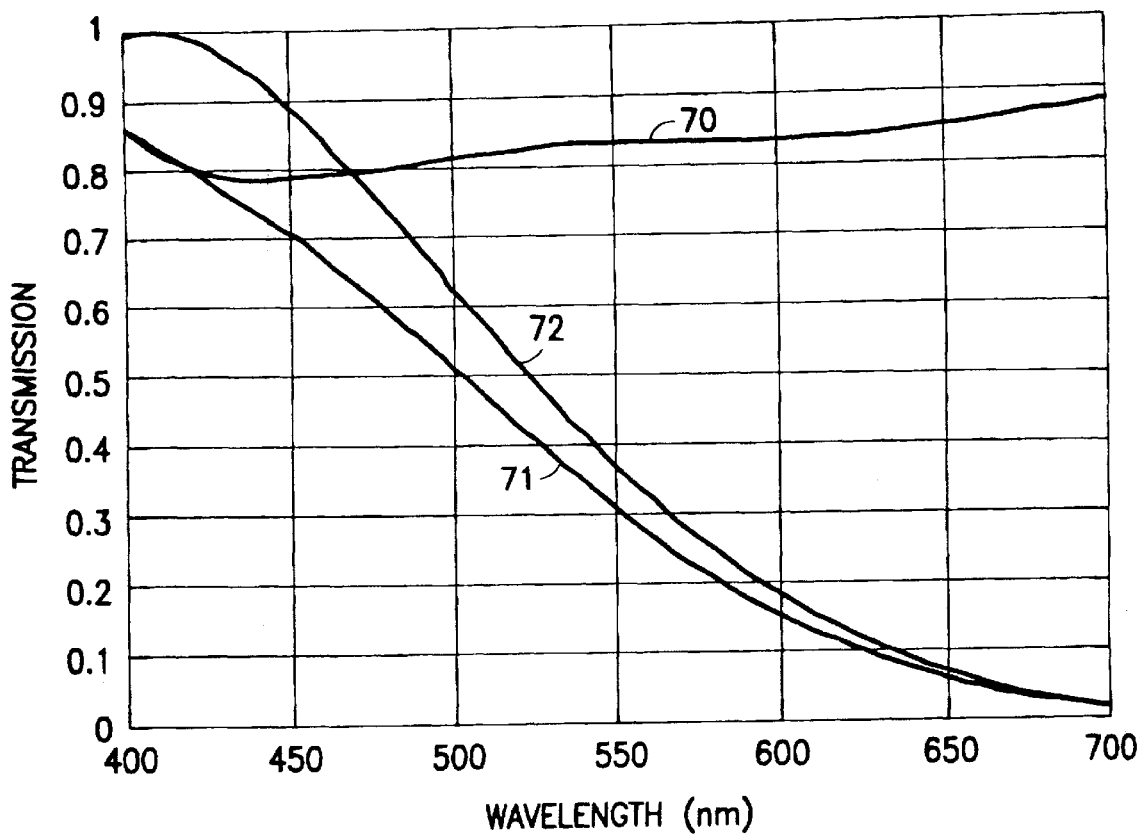
FIG. 5b shows the transmission of this LCTF at two different drive levels.

FIG. 5a shows an LCTF 58 suitable for practicing the present Invention. consisting of a pair of substrates 61 and 62, the inner surfaces of which have transparent electrodes 63 and 64, surrounding a liquid crystal layer 65. Collectively, these form liquid crystal cell 60. A birefringent film compensator 67 is adjacent the cell. At the entrance and exit of the arrangement are polarizers 68 and 69. One preferred embodiment uses a 5.5$\mu$ layer of liquid crystal material MLC-6648, the inner surfaces of which are treated to produce an antiparallel alignment of liquid crystal material 65 at the surfaces 63 and 64, yielding what is commonly known in the art as a flat-field cell. The liquid crystal director is oriented at 45° relative to the transmission axis of entrance polarizer 68, which is parallel to the transmission axis of polarizer 69. Substrate material is Corning 7059, 0.7 mm thick, and the ITO is magnetron-sputtered to a conductivity of 1000 $\Omega$/square. The compensation film 67 is omitted, as its purpose is to reduce the amount of residual retardance of cell 66 when fully driven, which is already quite low in this embodiment. Polarizers are die-cut Polatechno 18043P material. FIG. 5b shows the transmission of this LCTF with a square-wave signal of 18 Volts RMS applied as curve 70, and with no voltage applied as curve 71. The ratio is shown as curve 72.

In another preferred embodiment, the cell contains a 10$\mu$ layer of material MLC-6211, but is otherwise identical to the embodiment just described.

Another suitable optical arrangement for filtering the light is the birefringent interferometer described in "High-Performance Birefringent Imaging Interferometer" (P. Miller in Proc. SPIE 3920, "Spectral Imaging: Instruments, Applications, and Analysis", G. Bearman, D. Cabib, and R. Levenson, Eds., in press [2000]), when set to selected values of optical path delay (OPD). This instrument is an imaging interferometer based on liquid crystal elements, that produces continuously-variable optical path delay, depending on the voltages applied to the liquid crystal cells. Suitable values of OPD include zero, for an essentially clear transmissive state, and values of $\lambda/2$ or more. The latter produces transmission responses that are singly sloping, doubly sloping, or periodic functions of wavelength with many sinusoidal periods, depending on whether the OPD is small ($\lambda$ or less), moderate (one to two $\lambda$), or large (multiple $\lambda$). These states of various OPD can be used to constitute the different filter states of the present invention. Tuning is non-mechanical, and there is no displacement of the image in tuning.

Another liquid-crystal based interferometer is described by Sharp et. al. in "Liquid crystal Fourier transform spectrometer", (Sharp, Gary D.; Wang, Ping; Serati, Steven A.; Ewing, Teresa K., in Proc. SPIE Vol. 3384, p. 161–171, "Photonic Processing Technology and Applications II, Andrew R. Pirich; Michael A. Parker; Eds. [1998]). This produces discretely stepped values of OPD, rather than continuously-variable OPD. Again, by utilizing the zero OPD setting one can produce a clear state, while other values of OPD produce a singly-sloping filter response, doubly-sloping filter response, or filter responses that are periodic functions of wavelength, as described above.

Either of the liquid-crystal based interferometers has the property that the OPD is uniform across the field. That is, the spectral response imposed by the interferometer is substantially the same for all pixels in the image since they share the same OPD. In contrast, the mechanically-stepped SPECTRACUBE system based on the Sagnac design, made by Applied Spectral Imaging of Migdal Haemek, Israel provides a slightly different OPD at different points in the image. Consequently, it requires many exposures to determine how each pixel would appear under conditions of a specified OPD. While it might be possible to build a system along the lines of the present invention based on such an interferometer, where different filter functions are present at different spatial points, and consequently different intensity ratios are used for purposes of determining which probe is present, this would be more complex and is to be avoided if possible. Also, the zero-OPD case is a benefit in focusing and as a nominally unfiltered state; lack of such a state deprives one of these benefits. For these reasons, it is preferable that in embodiments that utilize an imaging interferometer to produce the filter responses, the interferometer should be a type that inherently expresses a fixed OPD at all points in the image, or should be modified to achieve this end if possible.

Figure 14:
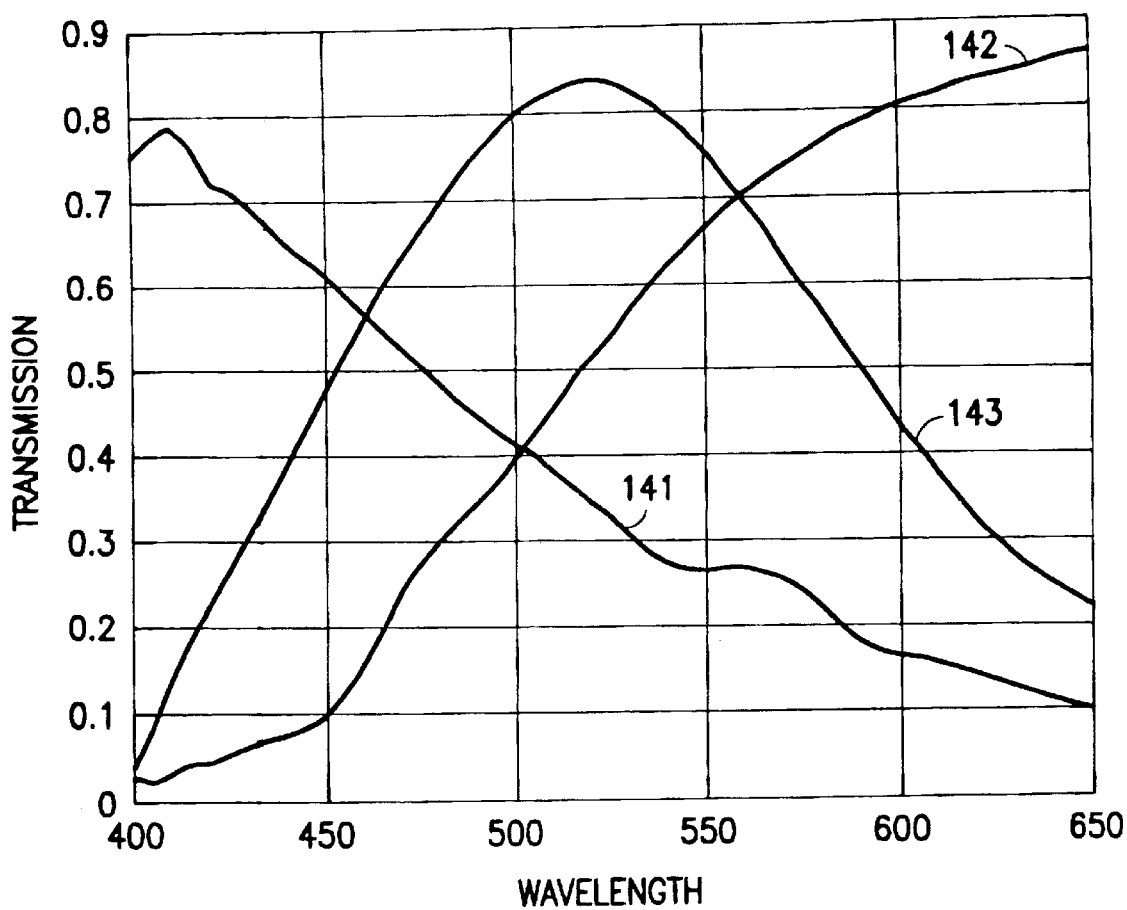
FIG. 14 shows the transmission of several colored filter glasses that may be useful in practicing this invention.

Yet another approach to filtering the light is to utilize discrete filters, such as colored glass filters from Schott Glass Technologies (Duryea, Pa.). FIG. 14 shows the response of a 2 mm thickness of BG34 glass, shown as 141, a 1 mm thickness of FG13, shown as 142, and a 1 mm thickness of VG6, shown as 143. The BG34 and FG13 glasses provide decreasing and increasing linear ramp functions of $\lambda$ over the range 400–650 nm, while the VG6 exhibits a doubly-sloped function with a peak in middle of the range. Filters such as these are suitable for practicing the present invention when placed in a filter wheel or the equivalent, which may also have one of the positions empty so that light of all wavelengths is transmitted in one selected state. Other filter elements may be used, such as dielectric-type filters, dyed plastics and cellophanes. Another suitable choice would be a retarder such as a 0.75 mm thick x-cut planar window of crystalline quartz from VLOC (Port Richey, Fla.) between parallel or crossed linear polarizers (Meadowlark Optics, Longmont, Colo.). This produces a transmission that is a periodic, sinusoidal function of $\lambda$.

When using a filter wheel, the various filters each introduce a slightly different optical wedge, and the effect is that the image shifts slightly as the filters are interchanged. However, because the filters are not bandpass-type, but rather exhibit a varying, nonzero transmission over a broad range of wavelengths, a given probe will be visible in more than one filter setting. In a preferred embodiment, one of the settings has no filter in the filter wheel and light is unfiltered except perhaps by a blocking filter which may be used to prevent stray excitation light from passing through to the detector. Such a blocking filter, if present, is preferably placed in some common portion of the optical path so as to be engaged for all settings of the filter wheel. When an unfiltered setting is used, light from all probes is presented to the detector, which thus forms an image of all probes at once. Images taken in one of the filtered states can be spatially registered with the unfiltered image by software, since any probes which are visible in a filtered state are of necessity also present in the unfiltered image. There is no problem spatially registering the two images, by means of the many well-known algorithms such as maximizing the cross-correlation function between the two. By registering each filtered image against the unfiltered image, they are all brought into mutual registration, even though for two given filter states, it may be that there are no probes visible at high transmission in both images.

It is a general property of this Invention that the filter shapes are not bandpass-type nor multipass-type, but instead are a sloping type across the range of at which the probes emit light. So, the same approach may be used even when there is no clear or unfiltered state, by registering pairs of planes that share a common probe, for as many probes as necessary until all planes are in mutual registration. The use of sloping-type filters, rather than bandpass-type filters, makes this possible.

Thus there is no need to incorporate multiply-tagged elements in the field of view for purposes of registering images, as is normally required by the prior art when high spatial fidelity is required.

From the above discussion it is clear that filter means useful in practicing this invention can be drawn from a wide range of technologies, including liquid crystal switchable filters as described in the above-mentioned patent "Tunable Optical Filter with White State"; liquid crystal cells with continuously or discretely variable retardance placed between parallel or crossed polarizers; interferometers that produce either a continuously or discretely tunable optical path delay; a filter wheel that may have an empty position with no filter while other positions contain filters of various types such as colored glass, dielectric filters, colored gels or plastics, fixed retarders between parallel or crossed polarizers, and combinations of these; and other filter means that produce substantially the same result.

In all cases, the key to the invention is that the filter means provide a set of spectral responses that are not conventional bandpass filters such as exhibit a well-defined passband, with high peak transmission in-band and a rapid transition to a low transmission out-of-band. It is not possible to practice the invention using such filters exclusively, regardless of whether the bandpasses are discrete or partially overlapping. Rather, at least one of the filters must have a spectral response that is slowly varying, sloping, or is a periodic function of wavelength. Its transmission varies from low to high (or vice versa) in a gradual and controlled fashion. The determination of which probe is present comes from measuring exactly where a given probe lies along a filter response slope that spans more than one probe. There must be at least one filter state of this type, which has a bandwidth that is spectrally broader than the principal emission band for a single probe, and which has a non-bandpass shape.

Figure 6:
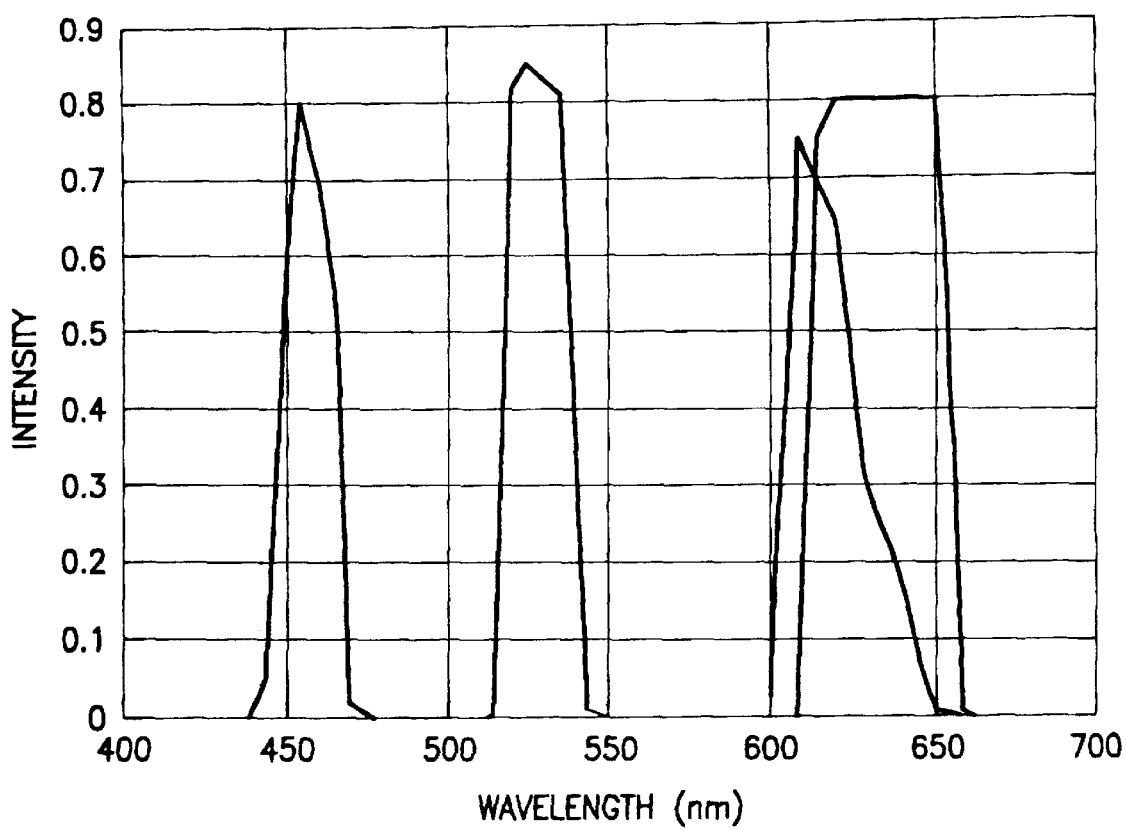
FIG. 6 shows the emission spectra of fluorescent probes DAPI, fluoroscein isothiocyanate (FITC), rhodamine, and Texas Red isothiocyanate (TRITC), excited using a triple-bandpass excitation filter and viewed through a corresponding triple-bandpass emission filter and dichroic element.
Figure 7:
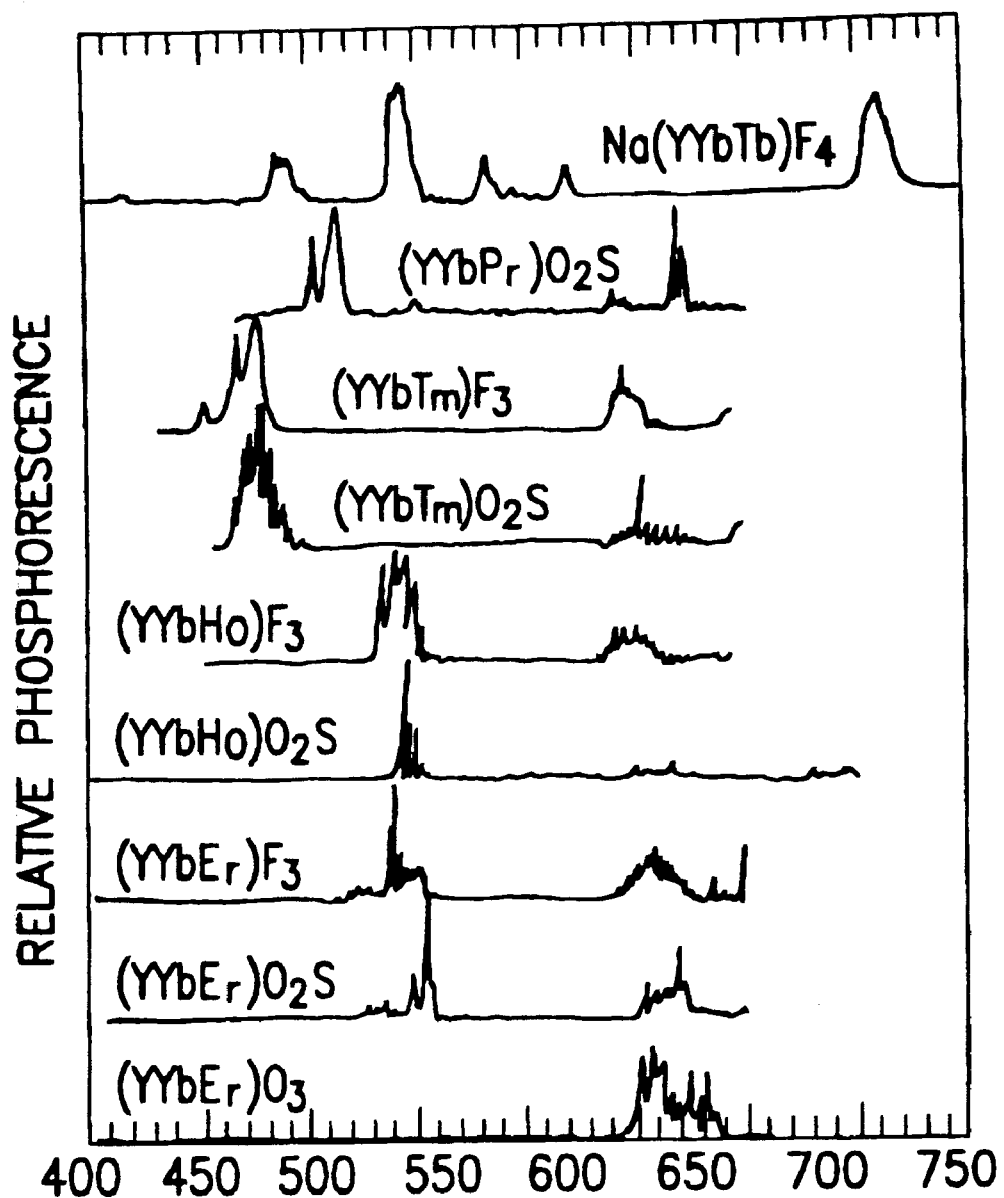
FIG. 7 shows the emission spectra of several up-converting probe species when excited in the infrared and imaged using a short-pass filter.
Figure 8:
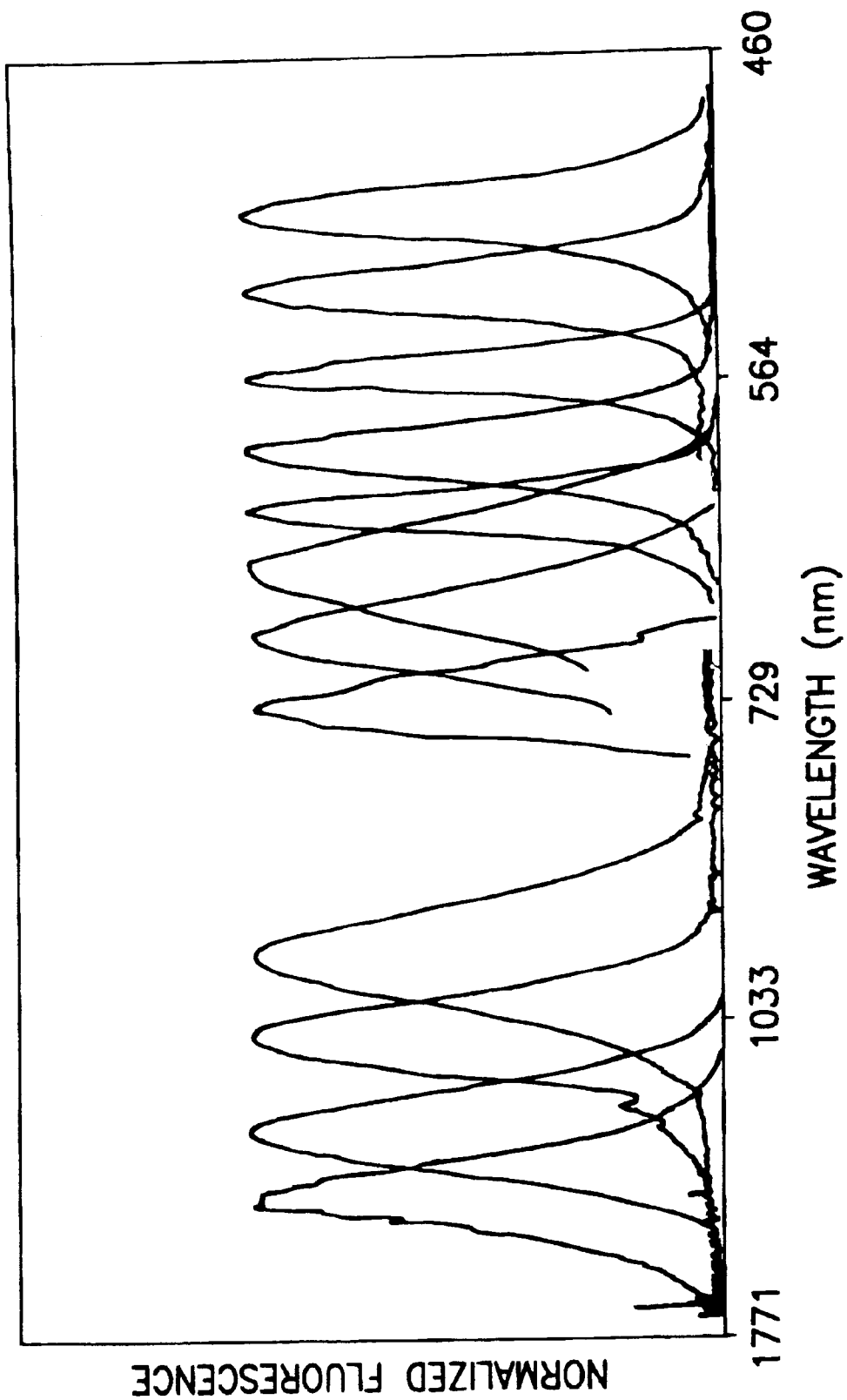
FIG. 8 shows the emission spectra of several quantum dot probes.

Curves of various popular fluorescent probes available from Molecular Probes (Eugene, Oreg.) are given in FIG. 6, and of various up-converting reporter probes available from STC (Bethleham, Pa.) as described in U.S. Pat. No. 5,736,410 and shown in FIG. 7. Quantum dot probes can be fabricated in forms which render them suitable for use as biological probes, with a wide variety of emission wavelengths, as described by W. C. Chan in Science, Sep. 25, 1998; 281(5385):2016–8 and M. Bruchez Jr. in Science, Sep. 25, 1988;281(5385):2013–6 and shown in FIG. 8.

Using multiple fluorescent probes often requires providing light in multiple excitation bands, as generally only a few probes can be excited at a given excitation band. It also requires isolation of the excitation light from the detector system. This is typically achieved using interference filters designed for multiprobe use, and commercially available from Chroma or Omega (both of Brattleboro, Vt.). Other approaches to eliminating excitation light from the sample emission, such as darkfield illumination or the use of polarizing beamsplitter cubes as epi-elements as taught by Hoyt et. al. in U.S. Pat. No. 5,943,129, could also be employed. Multiprobe work using downconversion phosphors is simpler, since typically all species of probes may be excited by a single infrared source, which is easily blocked using a interference-type barrier filter. Similarly, quantum dot probes are all excited in the UV or deep blue, which is readily excluded from the detector using a colored-glass filter from Schott (Duryea, Pa.) such as GG405, or other UV-cut filters that are well-known in the art.

As the previous Figures illustrate, the emissions from any given probe species are not monochromatic, but have a range of wavelengths. The effect of this on the present invention is that the system responds according to the integrated response across the range of emission wavelengths, viz. the response in filter state k to probe species j is:

$$E_{jk} = \text{(integral of) } T_k(\lambda) * I_j(\lambda) * S(\lambda) d\lambda \qquad [5]$$

where:

$T_k(\lambda)$ is the filter transmission in state k, at wavelength $\lambda$;

$I_j(\lambda)$ is the intensity of emission of the j-th probe, at wavelength $\lambda$;

$S(\lambda)$ is the response of the optical system and detector at wavelength $\lambda$;

and the expression is integrated over all $\lambda$ for which the probe has non-zero emission. The result is that the system experiences a first response $E_{j1}$ in the first filter state, and a second response $E_{j2}$ in the second filter state, the ratio of which is characteristic of a given probe species j and is unique amongst all species being imaged in a given experiment. Thus there is no practical difference in the system operation between this and the idealized case of monochromatic probe emissions. Even if the emission spectrum of a given probe species has a bi-modal distribution, the system works well, so long as the spectrum is systematic and reproducible.

Figure 9:
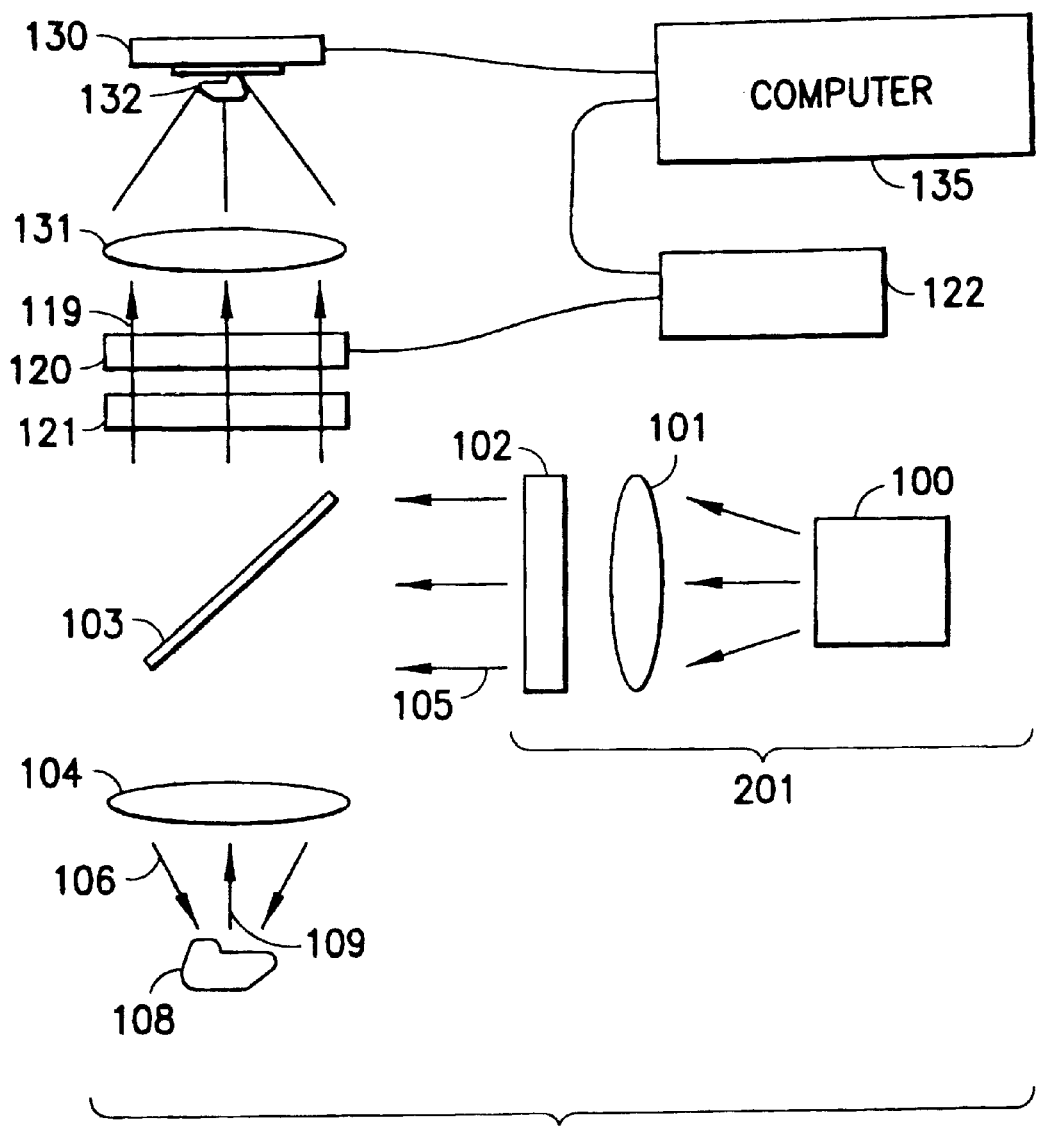
FIG. 9 shows a system for practicing the present invention using an LCTF.
Figure 10:
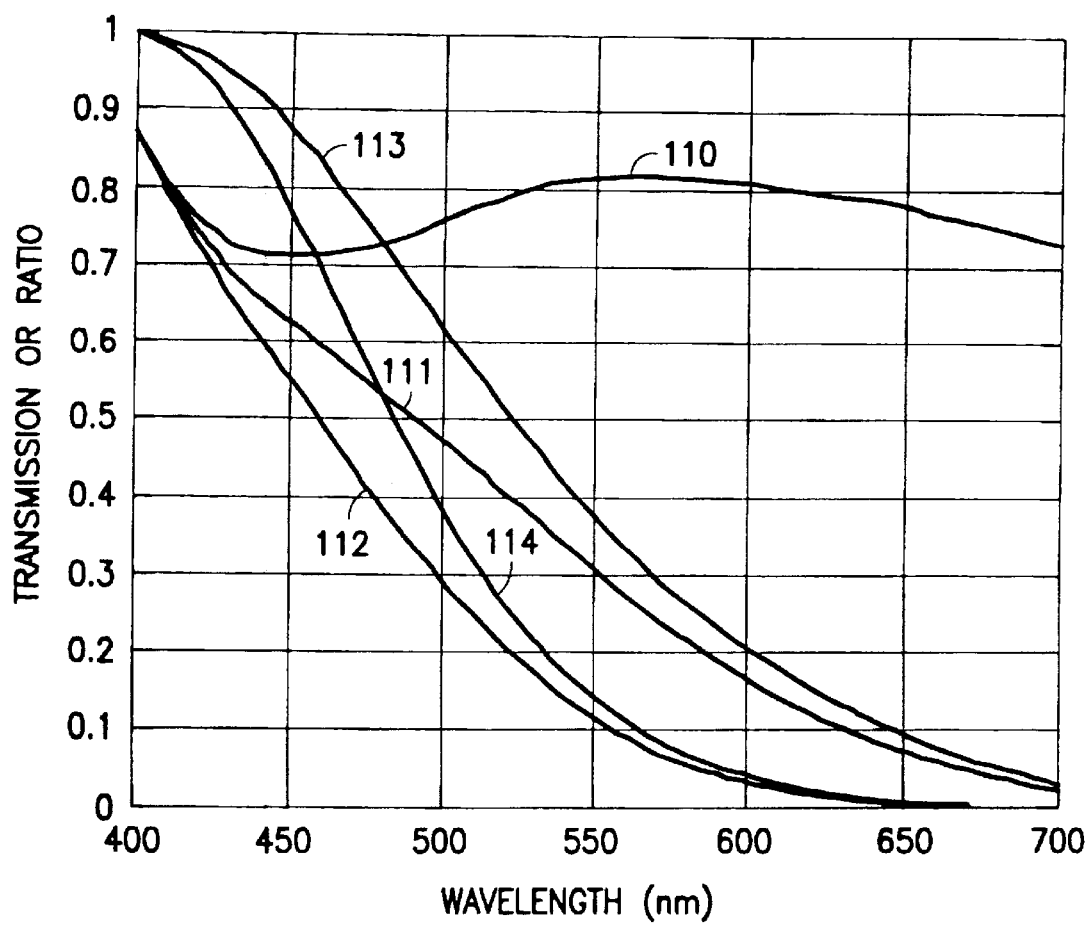
FIG. 10 shows the transmission T and transmission ratios for a three-state filter suitable for identifying when a mixture of probes, rather than a single pure probe, is present in a given pixel.

An overall system for imaging according to the present invention is pictured in FIG. 9, comprising an illumination system 201, a sample 108, a filter 120, and an imaging detector 130. The illumination system 201 comprises a source of excitation light 100, illumination optics 101, and excitation filter 102. Further elements include an epi-illumination element 103, and a primary objective 104 which deliver a beam of excitation light 106 to the sample 110. The objective also collects emission 109 from the sample to form a beam 119 which passes through blocking filter 121 and then to the tunable filter 120. Image-forming optics 131 produce an image 132 of the sample at the detector 130, which is connected to computer 135 which receives a digitized version of the image at the detector, and controls the tunable filter 120 through electronic control means 122.

In one preferred embodiment, the excitation light, optics, and objective are comprised of a Zeiss Axioplan II microscope with an Atto-Arc lamp source. Epi-element 103 is a polarizing beamsplitter from Karl Lambrecht (Chicago, Ill.) installed into the filter wheel component of the Axioplan. Tunable filter 120 is comprised of the LCTF described in connection with FIG. 1a and 1b. The detector is KX-085 cooled digital CCD camera from Apogee Instruments (Tucson, Ariz.), and the computer is a PC-type containing the Apogee Instruments interface card to receive the digitized images. The electronic control means are the MicroColor liquid crystal tunable filter electronics from CRI (Boston, Mass.), connected to the serial port of the computer. The excitation filter and blocking filter depend on the sample and probe species being imaged. In this embodiment, they are a DAPI/FITC/Rhodamine/Texas Red set from Chroma (Brattleboro, Vt.). The sample contains all four species.

In yet another embodiment, the excitation lamp is a mercury lamp, and the excitation filter is an interference filter which selectively transmits the 365 nm emission line. Epi-element is a UV reflector with maximum visible transmission, and the blocking filter is a piece of GG-405 absorptive glass from Schott Corp. The sample contains quantum dot probes with various diameters; these constitute different species with different emission wavelengths. All other elements are the same as in the previous example.

In another embodiment, the excitation lamp is a laser and the excitation optics are a collimator and various mirrors used to position the beam at the sample region being imaged. The epi-element is a holographic edge filter from Kaiser Optical (Ann Arbor, Mich.) operated at 5° incidence instead of the 45° incidence drawn, which reflects the laser beam with very high efficiency and transmits all light with wavelength greater than approximately 5 nm above that of the laser. A long-pass dichroic filter is used as the barrier filter, or this component may be omitted, depending upon the performance requirements, due to the high effectiveness of the holographic edge filter. Preferably, the SuperNotch variety is used to obtain narrower filter action, with blocking of optical density 4 or higher. A conventional objective is used, and the detector, computer, and filter control means are the same as listed in the previous embodiments.

A fourth embodiment uses an infrared diode laser emitting at 940 nm as the excitation source; the epi-element and blocking filter reflect that wavelength while transmitting light with wavelengths $\lambda<630$ nm. The sample is tagged with various probe species of up-converting reporter.

A fifth embodiment uses no illumination system 201 nor epi-illumination element 103 because the sample is bioluminescent, chemiluminescent, or otherwise luminous without need for an excitation light source.

A sixth embodiment uses a camera which contains three separate CCD detectors mounted with a trichroic prism. Means for assembling multiple CCD detectors with a common boresight are well-known in the art, and are used in high-end RGB cameras for video and scientific imaging. Or, firms such as Richter Enterprises (Wayland, Mass.) will design custom cameras of this type upon request. In this embodiment, the camera is a standard commercial RGB camera of this type, the Model DXC950 from Sony Corporation of America (Park Ridge, N.J.). Its trichroic prism directs red light to a first CCD detector, green light to a second CCD detector, and blue light to a third CCD detector. The images acquired by the three color planes are read out simultaneously with three sets of electronics within the camera fed to a three-channel RGB frame grabber. The detectors and prism optics are spatially registered at the time of manufacture so the same point in space is imaged to the same location on each of the three CCD detectors, to within approximately one pixel. This arrangement enables detection of probes in three color bands at the same time. It is used with filter means identical to those whose response is pictured in FIG. 2, except that they are constructed with 130 micron layers of PVA instead of 145 micron layers. This alteration shifts all the spectral features slightly towards shorter wavelengths. In the blue band, which extends from generally 420 nm–485 nm, the ratio of filter responses is monotonically decreasing with wavelength. In the green band, which extends from 490–585 nm, the ratio of filter responses is monotonically increasing with wavelength. In the red band, above 585 nm, the ratio of filter responses is flat until approximately 610 nm, above which it is monotonically decreasing.

Note that although the camera has three detectors, only one filter element is required and it may be placed anywhere in the optical path between the emissive sources and the camera, where it is separated by the trichroic into three beams, each of which is spectrally distinct and is sent to a separate CCD detector. Within a given color band, the ratio of filter responses is monotonic and various probes can be determined without ambiguity. The probes are preferably chosen so the emission from any given probe lies entirely or principally within a single primary color band. By taking a pair of images, and looking at the ratio of signal responses at each detector, the species can be determined unambiguously.

This type of system detector has the obvious benefit that the trichroic element directs emissions that are widely-separated in spectral response to different detectors, which enables sensing up to three spatially colocalized probes and resolving the identity of each one independently. For experiments that may produce colocalized probes, or which require combinatorial labeling, this extends the present invention from the identification and quantification of single probes per pixel to multiple probes per pixel.

Another benefit of this embodiment is that the slope of the filter response can be approximately three times steeper and can have three times finer spectral period, compared to the filter response in a system that seeks to identify probes across the entire visible range. This is because it needs only to be unambiguous over the spectral range of a single band of the trichroic. As a result, one can resolve more probes, or probes that are quite densely spaced in their emissions.

The probe species is preferably determined by the ratio of the response at a given CCD detector in two or more filter states, rather than the ratio of response at one CCD detector versus the response at a different CCD detector. It is preferable when designing the experiment to choose emissive species that ensure this, when possible. The benefit this provides is that there is no need to take ratios between images obtained with different detectors. Thus minor misalignment between the CCD detectors does not undermine the integrity of the probe identification.

In yet another embodiment, a custom multi-CCD camera is used as the detector means, with a trichroic prism set that directs light having λ<540 nm to a first CCD detector, light having 540 nm<λ<660 nm to a second CCD detector, and 660 nm<λ<800 nm to a third CCD detector. Light in the spectral transition regions, i.e. near 540 nm and near 660 nm, is partially directed to two different detectors due to limitations in the coating art, which define a minimum cut-on and cut-of bandwidth. These limitations are typically somewhat more severe for the trichroic prism than for other filter devices because of the need to operate over a relatively wide range of wavelengths, and because at least one of the color bands is separated at surfaces encountered at non-normal incidence.

If desired, the beams can be subsequently filtered after separation by the trichroic prism, before they encounter the CCD detector for that channel. Filters for this purpose would typically be operated at normal incidence, and need only perform well over the spectral range of a single channel, rather than over the entire range of the instrument. Under these simpler constraints, a filter can be made with sharper cut-on and cut-off than the trichroic element provides. In the present example, it is possible to provide each channel with a spectral cut-on and cut-off that are as abrupt as 15 nm or less, although there is reduced efficiency over a somewhat wider range, since in the region near the cut-on and cut-of, some of the optical energy is misdirected by the dichroic to the spectrally-adjacent channel. High performance cut-on and cut-off filters are available from optical coating firms such as Chroma (Brattleboro, Vt.) or Omega (Brattleboro, Vt.).

The camera in this embodiment uses nominally identical CCD detectors and electronics for the three channels. The detectors may be Peltier-cooled as is well-known in the art if light levels are extremely low, but often this is not necessary given the high intrinsic efficiency of the present Invention. Suitable CCD detectors are well-known in the art.

Figure 15A:
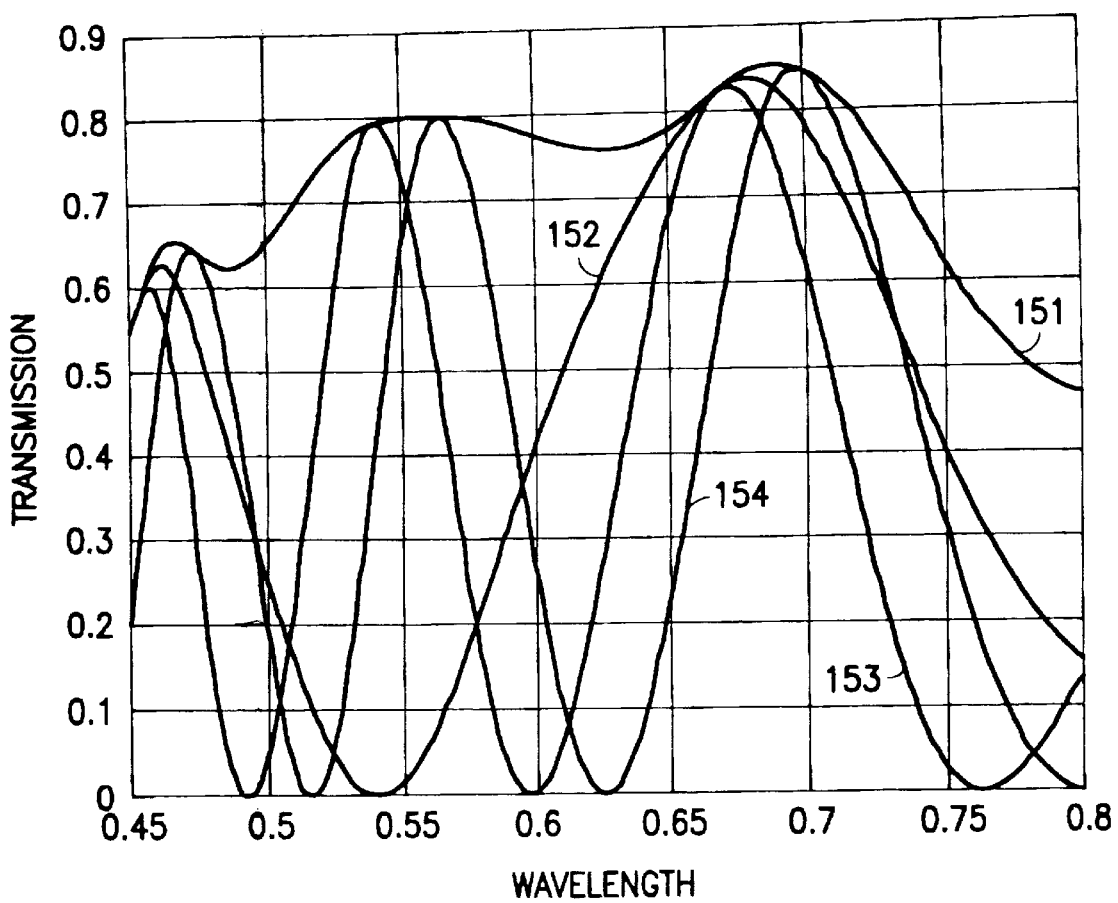
FIG. 15a shows the transmission of an LCTF in each of four filter states, one of which has a substantially neutral spectral response.
Figure 15B:
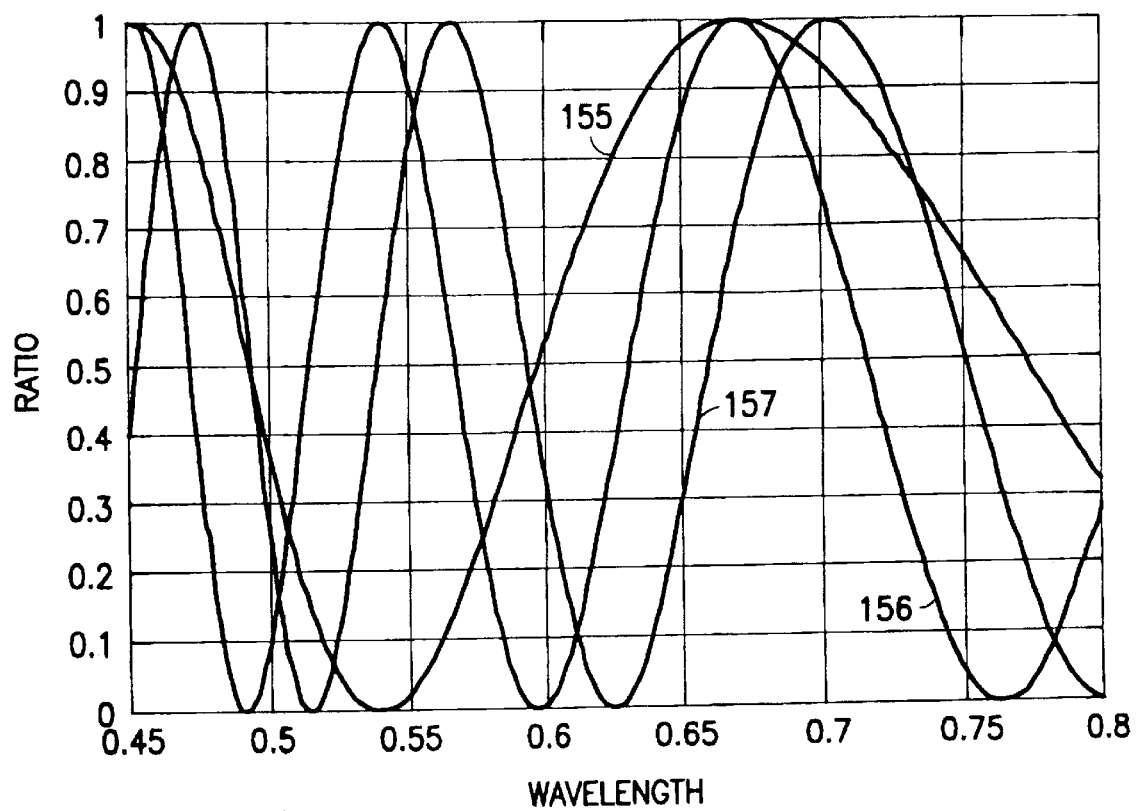
FIG. 15b shows the ratio of transmission between the three non-spectrally neutral filter states and the substantially neutral state.

The filter used in conjunction with this embodiment consists of three stacked liquid crystal filter stages. Each stage comprises a variable retardance liquid crystal cell with its buffing axis at 0°, sandwiched between a pair of retarders made of NRZ film (Nitto Denko, Fremont, Calif.) with their slow axis oriented at 45°. The liquid crystal cells yield a retardance of λ/2 for 570 nm light when undriven, and a retardance of approximately 10 nm when driven with 15 Volts at a frequency of 2 kHz. Each retarder in stage 1 is a single sheet of NRZ-650 film, while each retarder in stage 2 is two sheets of NRZ-650 in series, and each retarder in stage 3 is two sheets of NRZ-684 in series. There is a Polaroid HN38S polarizer before the first stage, between each stage, and after the last stage; all have their transmission axis at 0°. When all cells are undriven, the overall response is highly transmissive over this range. As one cell at a time is driven while the other two are undriven, three different and strongly filtering responses are produced. The transmissive state 151 and the three filter states 152, 153, and 154 are shown in FIG. 15a, and the ratio of filtering states to the transmissive state is shown in FIG. 15b.

The filters are designed so that the ratio of the first filtering state to the transmissive state, shown as 155, reveals the approximate wavelength of the emission, while the ratio of the response in the second state and third state to the transmissive state, shown as 156 and 157 respectively, determine it very precisely. The latter two filter states have approximately the same spectral period, but are shifted in phase by approximately one-quarter wave. Thus, when the filter state 153 has a peak or minimum in its sinusoidal response, at which point its slope is zero and it yields little wavelength information, the filter state shown as 154 is at or near its inflection point where it has maximum slope, and vice versa. Thus the overall measurement will rely on one or the other of these filter states to make the fine determination of wavelength, depending on the wavelength of the probe involved. For these purposes, the coarse measure provided by the first filter state 152 is adequate to determine which of the second or third states, 153 and 154, carries more information. Or, the ratio measure of the intensity sensed during the second and third states may be used: if it is nearly 100% or 0% for a given state, the other state may be preferable for identifying that probe.

In this way, one can determine the identity of triply labeled samples or combinatorial probes with up to three spatially colocalized emissions. The system is capable of resolving wavelengths to within 2 nm. This is realized by achieving a signal-to-noise of 25:1 in the ratio images, and having a slope in the filter response of 100% per 50 nm. For probes such as quantum dots, which can be manufactured with precisely-controlled emission wavelength, it is possible to resolve which species is present from among a choice of 30 or more probes per band, in each of the three bands simultaneously. Overall, a total of 30×30×30=27,000 different combinations can be uniquely tagged and identified. Only four exposures are required, leading to very high throughput.

It is possible to construct a system that achieves resolution of 4 to 5 nm in assigning wavelength or probe species, using only the broadest filter element from this embodiment. This still enables identifying probes from among at least 8 and typically 15 or more possible species in each band, and requires only a pair of exposures per sample to identify up to three colocalized probes per pixel. This results in a total of approximately 15×15×15=3125 different combinations.

The optical efficiency of this system is quite high. The multiple-detector CCD directs approximately 80% of the incident light to one of its detectors, and a single-stage liquid crystal tunable filter has efficiency of 85% or more. Further, the use of broad sloping filter responses rather than narrow bandpass responses means that the full spectral emission of the probe is utilized. Thus, it is a strong contender for use in high-throughput screening, pharmacogenomics, and other applications that must process lots of samples in a short time, or where flux levels are inherently low.

While the same benefit can be realized with the present invention using a monochrome camera and taking three sets of variously filtered exposures while red, green, and blue filters are introduced into the optical path, the use of a multiple-CCD camera has performance advantages of speed, optical efficiency, simplicity, and absence of moving parts.

In some applications, the nature of the sample dictates that only a single probe species can be present at any given location, and hence each pixel in the sensor will only receive emissions from a single species of probe. For these applications, the filters described above in the first five embodiments are suitable for making a species determination directly from the ratio $E_2/E_1$ without ambiguity. However, when a given sample location may emit light from two or more probes in an unknown proportion, and there are no further spectral selection means (such as the trichroic prism in a multiple-CCD camera), it is possible to misidentify the resultant mixture as another species entirely.

To illustrate this, consider an example where the filter states $T_1$ and $T_2$ are as given in FIG. 1b, and the probes emit at wavelengths 450, 500, 550, and 600 nm. For simplicity, the detector is a monochrome type whose responsivity in this example is uniform with $\lambda$ across the range. However, the problem is a general one, and could occur for a variety of filter shapes, detectors, and probe species. In this example, the table of emission strengths and target ratios for each probe, and the target ratio used for detection is:

TABLE 1

| Probe | $\lambda$ | $T_1$ | $T_2$ | Target ratio $E_2/E_1$ |
|---|---|---|---|---|
| A | 450 | 0.81 | 0.72 | 0.87 |
| B | 500 | 0.84 | 0.52 | 0.62 |
| C | 550 | 0.87 | 0.33 | 0.37 |
| D | 600 | 0.87 | 0.18 | 0.21 |

Equal, unit fluxes from probe A and C will result in a reading of 1.68 in filter setting 1 and a reading of 1.05 in filter setting 2, with a $E_2/E_1$ ratio of 0.625 which is nearly identical to that of species B. This pixel would be identified as containing species B, when in actuality it contains species A and C. Or, consider the case where a pixel emits one unit of flux from probe A and 0.6 units of flux from probe D will yield a total reading of 1.332 in filter state 1, and 0.828 in filter state 2, with a $E_2/E_1$ ratio of 0.621. Again, it will be mis-identified as containing species B. Comparable examples can be constructed that mimic C from mixtures of A and D, or of B and D. Fractional amounts of a species can be encountered for a number of reasons, such as e.g. different concentration in the sample; a species being at a slightly different height within the sample and thus out of focus; or other factors which cause it to be sensed with different efficiency than another species.

The present Invention contains means for recognizing the presence of such ambiguity, and resolving it correctly when two probe species are present in a given pixel. FIG. illustrates the transmission of a filter with three states: a first state 110 with high transmission at all wavelengths; a second state 111 which decreases monotonically with wavelength; and a third state 112 which also decreases monotonically with wavelength, but more rapidly than state 111. This filter may be constructed by placing two elements as per FIG. 1a in optical sequence. When both liquid crystal cells are undriven, state 110 results; driving one while the other is undriven produces 111, and driving both produces state 112. The ratio of transmission in state 111 to 110 is shown as ratio 113, and the ratio of transmission in state 112 to 110 is shown as ratio 114. The ratios $T_2/T_1$ and $T_3/T_1$ are shown as 113 and 114, respectively.

Comparing this against the mixtures from the previous example, the mixtures produce ratios $E_2/E_1$ which mimic species B, but their ratios $E_3/E_1$ differ from that of B, so the ambiguity is identified. Specifically, the table for this new set, including the state $T_3$ is now given

TABLE 2

| | $\lambda$ | | | Target ratios | |
| Probe | (nm) | $T_1$ | $T_2$ | $T_3$ | $E_2/E_1$ | $E_3/E_1$ |
|---|---|---|---|---|---|---|
| A | 450 | 0.81 | 0.72 | 0.62 | 0.87 | 0.76 |
| B | 500 | 0.84 | 0.52 | 0.32 | 0.62 | 0.38 |
| C | 550 | 0.87 | 0.33 | 0.12 | 0.37 | 0.14 |
| D | 600 | 0.87 | 0.18 | 0.04 | 0.21 | 0.04 |

The first case of equal unit fluxes of A and C produces a reading of 1.68 in filter state 1, 1.05 in filter state 2, and 0.74 in filter state 3. As shown above, the ratio $E_2/E_1$ for the mixture matches that of pure species B, but the ratio $E_3/E_1$ is $(0.74/1.68)=0.44$, which is readily detected as different from the target of 0.38 for pure species B. The second case, unit flux of A and 0.6 flux of D, produces a ratio $E_3/E_1$ of $(0.644/1.332)=0.48$, at even greater disparity from that of pure species B.

The mechanism can be seen directly, that since filter state 3 is the result of two identical filter elements in series, its wavelength dependence of $T(\lambda)$ is approximately that of filter state 2, squared. No mixture of emission wavelengths can satisfy the relationship that their linear combination matches that of another pure species, while at the same time matching it for a quadratic function. Any nonlinearity will produce this effect, but to achieve maximum discrimination, the filter states should be chosen to maximize the disparity, as would be obvious to one skilled in data analysis and equipment design.

Figure 11:
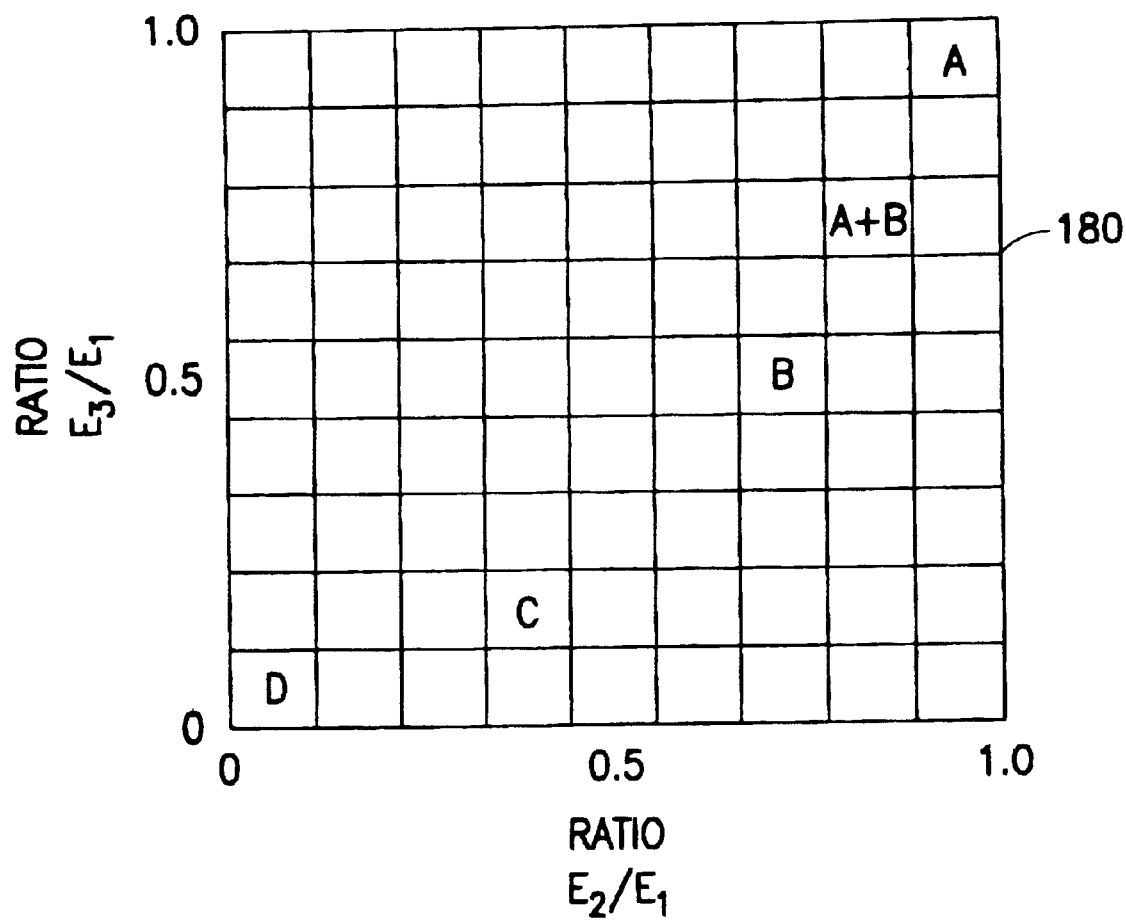
FIG. 11 illustrates a lookup-table for determining the species present at a given pixel.

FIG. 11 illustrates a lookup-table 180 for determining the species from among a families of species which may be present at a given pixel, using the readings $E_1$, $E_2$, and $E_3$, obtained in three different LCTF states. The column corresponds to the ratio $E_2/E_1$, and the row corresponds to the ratio $E_3/E_1$. Pixels containing a single pure species have a single characteristic value for each ratio, so the contents of the table at the [row, column] location corresponding to these ratios will be programmed to indicate a single pure species. Pixels containing a mixture of two or more species can present a variety of ratios, depending on the relative proportions of the species involved; thus several table entries will exist for each possible mixture, spanning the various mixing proportions and listing for each entry the proportion of each component present. However, the filter states may be chosen so that no 'mixed' state entry has the same [row, column] address as a pure species, as discussed in the previous section. Thus attribution of species is unambiguous.

There may be a number of unpopulated table entries, for which no single species nor mixture produces the corresponding set of ratios $E_2/E_1$ and $E_3/E_1$. If the observed ratios correspond to an unpopulated entry, it indicates a defect in the data, or the presence of other unexpected agents. This provides an internal data quality measure, and allows defective points to be identified.

It is appropriate to allow for noise in the readings when assembling the look-up table, as is conventional in the art. For example, the entry for a single pure species is preferably provided at several table addresses, comprising the entry for the exact ratios $[E_2/E_1, E_3/E_1]$ and for entries in the neighborhood, at adjacent rows and columns. This ensures that when readings differ slightly from the ideal values, the table will nonetheless indicate the proper species. The size of the included neighborhood effectively defines the tolerance before a reading is said to be defective, and will be chosen in light of actual signal-to-noise levels, to insure robust operation.

Figure 12:
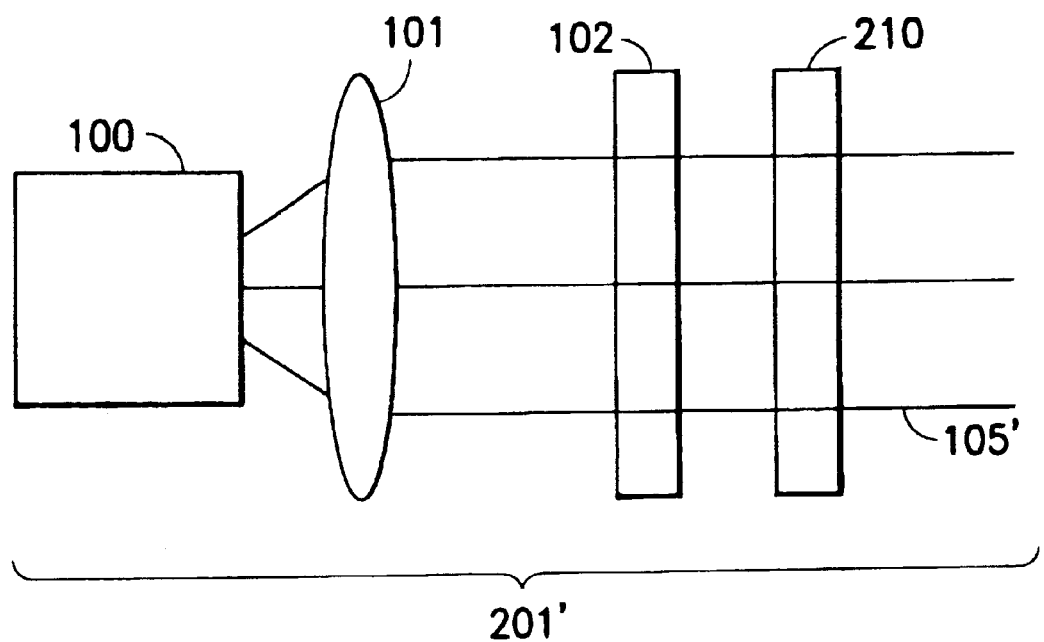
FIG. 12 shows illumination optics incorporating a fixed shaping filter in addition to the excitation filter.

FIG. 12 shows illumination system 201' incorporating a fixed shaping filter 210 in addition to the lamp, lamp optics, and excitation filter. This element alters the relative proportion of spectral components in the excitation beam, to control the relative excitation of different species in the sample. It may be necessary to provide a greater or lesser degree of excitation to different probe species, due to differing brightness properties of the probes involved. If one probe species produces significantly greater signals at the photodetector than the other species, there will be an overall disparity in exposure levels between pixels containing different species. While some degree of disparity is normal and acceptable, it degrades the signal-to-noise of the dimmer species, and it may be preferable to reduce the excitation of the brighter species so that a more balanced exposure is possible. Fixed shaping filter 210 provides the means for doing so. It may be a colored glass material, or a dielectric filter, or indeed any filter which provides the desired transmission properties without undue fluorescence emission of its own. If multiple laser sources are used, an equivalent measure is to adjust or regulate the relative intensity levels of the various laser beams.

A comparable situation may occur where the relative emission levels from several probe species are quite different. Then it may be useful to employ a fixed shaping filter to selectively attenuate the emissions from the brightest species, so that a more balanced exposure is obtained. This increases the signal-to-noise in resolving the dimmer species, which it does at the cost of some efficiency for the brightest species; however, the latter are by supposition relatively bright, and so easily detected.

The fixed shaping filters just described are to be employed in addition to whatever excitation, dichroic, and emission (barrier) filters are required to excite the sample and to restrict unwanted excitation light from the emission beam. However, it may on occasion be suitable to incorporate two such elements into a single component, such as to use an excitation filter which provides the sought-for ratio of excitation energies, without need for a distinct fixed shaping filter. These variations will depend on the specific apparatus and are solved using the conventional methods of the optical and microscopic arts.

Figure 13:
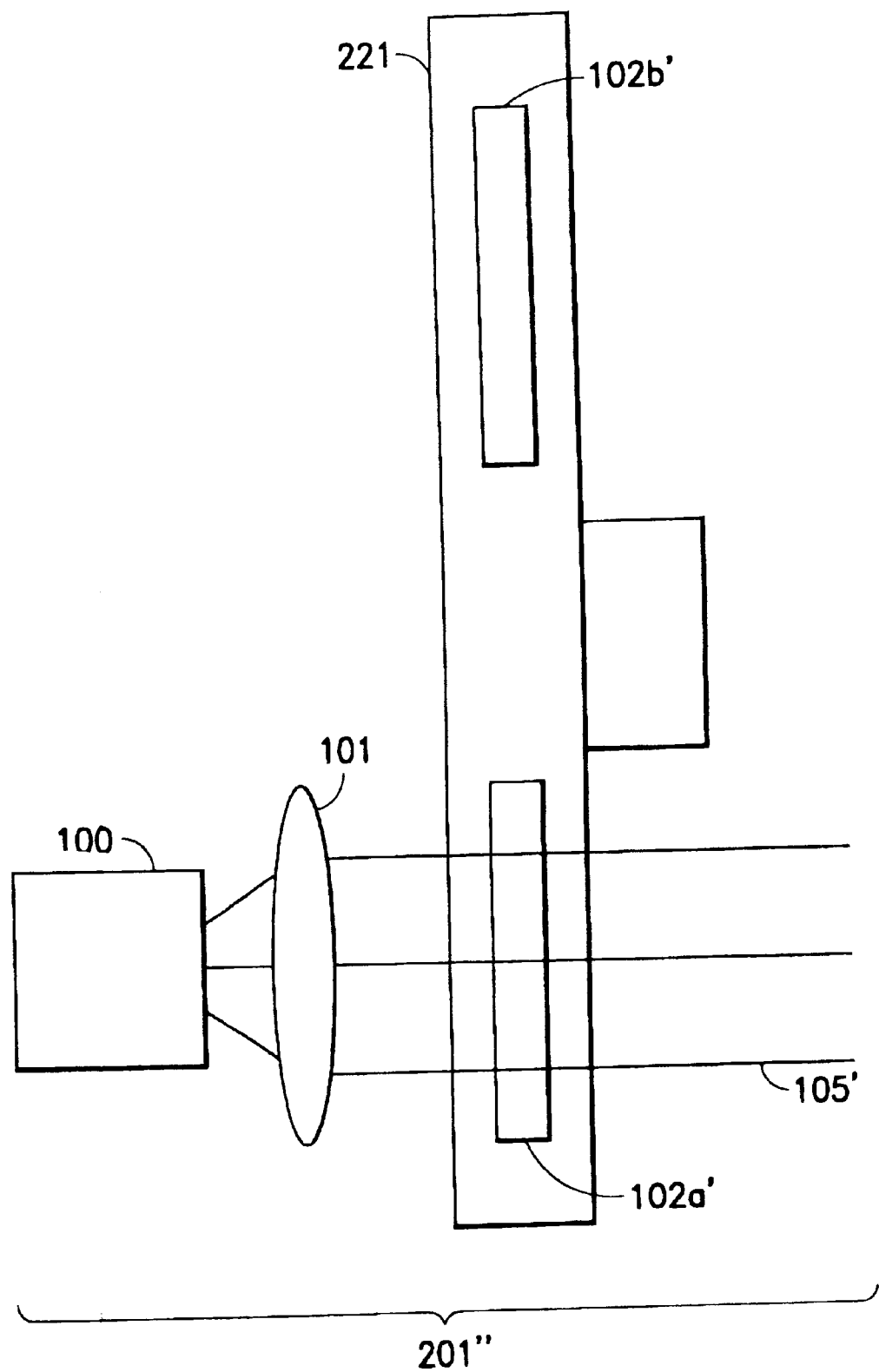
FIG. 13 shows illumination optics incorporating a filter wheel for selectable excitation.

FIG. 13 shows illumination optics 201" incorporating a filter wheel 221 for selectable excitation. This provides means for a variety of excitation bands, by cycling the filter wheel to a variety of settings. It may be preferred to take images at each LCTF setting, while holding the filter wheel in a fixed position; and then to advance to the next filter wheel position and take images at each LCTF setting; and so on. In this case, one obtains an image of the sample under single-excitation conditions for each excitation band, and the LCTF provides the means to separate several probe species per excitation band.

Or, one can take a single extended exposure at a given LCTF setting, while cycling the filter wheel to produce controlled times at each filter wheel setting during the exposure. The process would then be repeated for a second exposure at the next LCTF setting, and so on. This provides an image of the composite excitation provided by the various filter wheel settings, with the LCTF providing the means to separate several probes from the overall emissions. The filter wheel provides a means for equalizing the relative brightness of samples, comparable to that of the fixed shaping filter 210, by controlling the relative exposure time at each filter wheel setting. Exposure times must be well-controlled, so that comparable emissions are imaged in each LCTF exposure.

Another practical consideration is photobleaching. The accuracy of the ratios $E_2/E_1$ can be degraded since the sample may undergo photobleaching or other decay processes during the time required to take sequential exposures at a plurality of LCTF states. The effect of photobleaching is to understate the signal level of the later exposures. It may be preferable to take exposures in a sequence such as: $E_1, E_2, E_1', E_3, E_1''$. From readings $E_1$ and $E_1'$, one may determine an interpolated value corresponding to the expected reading $E_{1int}$ which would have been obtained at the intermediate time when exposure $E_2$ was obtained. If a simple average is used to interpolate $E_{1int}$, the ratios are then calculated as:

$$R_{21}=2*E_2/(E_1+E_1') \qquad [6a]$$

$$R_{31}=2*E_3/(E_1+E_1'') \qquad [6a]$$

More complex interpolation can be used to account for exponential decay and the like, to best approximate the decay processes for a given application, as is known in the art.

The present invention can be employed in a variety of settings, including without limitation dark-field, epi-illumination, fiber-probe, total-internal-reflection excitation, two-photon, and conventional microscopy. It may be used to image sample types including without limitation conventional microscopy samples, DNA chip arrays, capillaries, multiwell micro-titre plates, and electrophoresis gels. It may be used in concert with laser microscopy and confocal microscopy by placing the filter in front of the detector, then recording successive frames with the filter in its various settings. The filter only needs to change state once per complete scan. It is not necessary that the filter switch states at every pixel, unless this is sought for reasons such as improved time simultaneity. In this case, it may be preferable to construct the tunable filter using a rapidly responding liquid crystal switch such as a ferroelectric liquid crystal cell. These are known in the art, and use of them in tunable filters suitable for this invention is taught in the Miller et. al. U.S. Pat. No. 5,892,612, "Tunable Optical Filter with White State".

Where retarders have been shown, it is suitable to use any material which produces the desired optical effect, including without limitation stretched polymer films such as Mylar, polyvinyl alcohol, polycarbonate, nylon, cellophane, polyester, polyethylene terapthelate; oriented liquid crystal materials, liquid crystal polymers, photopolymerized liquid crystal polymers; birefringent crystals such as quartz, mica, calcite, lithium niobate, KDP, ADP; and any other material, laminate, assembly, structure, or composition of matter that produces optical retardance, as well as equivalents to those listed above, or combinations thereof.

Where polarizer materials have been shown, one may use sheet dichroic type such as those made by Polaroid (Norwood, Mass.), International Polarizer (Marlboro Mass.), Polatechno Co., Ltd. (Tokyo, Japan), Nitto Denko America (Fremont, Calif.), Sanritz (San Jose, Calif.); sheet reflective type such as that made by 3M (St. Paul, Minn.); spatially displacing type such as a Wollaston prism or doubly refractive calcite slab; critical angle type such as Glan-Thomson, Glan-Taylor, and the like; dielectric type polarizing beamsplitters such as those sold by Meadowlark Optics (Longmont, Colo.); oriented glass-silver matrix type such as Polarcor made by Corning Advanced Products (Corning, N.Y.); or any equivalents or combinations thereof.

Various embodiments have been shown which illustrate the use of the invention in the visible and near-visible, but it is within the scope of the invention to practice it in any spectral range that is necessary for a given application, including without limitation the near-ultraviolet, visible, and near-infrared.

The calculation and electronics means used in the invention include equipment to measure the intensity levels at the detector, to determine the ratio of relative intensity levels between images obtained in different filter states, and to identify the species of probe corresponding thereto. The intensity levels can be measured by digitization means within a digital camera, analog amplifiers or video circuitry in combination with an external digitizing frame-grabber, or circuitry integral to the detector such as in CMOS sensors that incorporate both detection and digitization functions, or any equivalent apparatus. Ratios can be determined by a general-purpose computer such as a PC, or by means of dedicated image ratio hardware, such as is available on certain frame-grabber boards, image processing boards, or custom circuitry constructed for this purpose. Similarly, the species identification can be performed by a general purpose computer such as a PC running software that implements the selection method described elsewhere in this application. Other means for doing so could included dedicated processor hardware including electronic or optical computers or correlators. The apparatus used for this may be any type provided that it achieves the functional purpose of species identification.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

We claim:

1. An imaging system for detecting and discriminating N different light emissive probes contained at a plurality of locations within a sample, the probes being capable of emitting at different wavelengths over a spectral range, said system comprising
   optics that receive light emitted by the probes and form an image of the sample,
   a pixelated photodetector that receives light comprising the image of the sample,
   filter means for selectively filtering the light received by the photodetector according to two or more different filter states, each filter state having a predetermined spectral response function,
   electronic means that records photodetector readings for each pixel while the filter means expresses M filter states from among the predetermined spectral response functions,
   calculation means for determining which probes are present at each point in the sample by comparing two or more of the photodetector readings obtained at different filter states,
   wherein the number of probes N which can be determined exceeds the number of expressed filter states M.

2. The system of claim 1 wherein the transmission band of at least one filter state is not bandpass in shape and is broader than the emission band of one of the emissive probes.

3. The system of claim 1 wherein the filter means comprises continuously a tunable liquid crystal filter element.

4. The system of claim 1 wherein the filter means comprises a switchable liquid crystal filter element that selects between discrete spectral response functions and is not continuously tunable.

5. The system of claim 1 wherein the number of expressed filter states M is three or more.

6. The system of claim 1 wherein one of the expressed filter states is substantially neutral in its spectral response.

7. The system of claim 1 wherein one of the expressed filter states has a spectral response function that is periodic in wavelength, and the spectral response function undergoes one or more periods over the spectral range in which the probes emit.

8. The system of claim 7 where a second of the expressed filter states has a spectral response function that is one of a monotonically increasing function of wavelength, a monotonically decreasing function of wavelength, and a periodic function with a half period or less, over the spectral range in which the probes emit.

9. The system of claim 1 further including a source of excitation light that stimulates optical emission by the probes in the sample.

10. The system of claim 9 further including means for spectrally filtering the excitation light to alter the balance of emission by the probes.

11. The system of claim 1 further including fixed filter means that imparts a spectral weighting function that is common to all photodetector readings.

12. An imaging system for detecting and discriminating different light emissive probes contained within a sample, the probes being capable of emitting at different wavelengths over a spectral range, said system comprising
   optics that receive light emitted by the probes and form an image of the sample,
   a pixelated photodetector that receives light comprising the image of the sample,
   filter means for selectively filtering the light received by the photodetector according to two or more different filter states, each filter state having a predetermined spectral response function,
   electronic means that records photodetector readings for each pixel while the filter means expresses different filter states from among the predetermined spectral response functions, and
   calculation means for determining which probes are present at each point in the sample by comparing two or more of the photodetector readings obtained at different filter states,
   wherein at least one of the expressed filter states is attenuative over at least a portion of the spectral range, and has a spectral response function that is not bandpass nor shortpass nor longpass type.

13. The system of claim 12 wherein at least one of the expressed filter states has a spectral response function that is not bandpass nor shortpass nor longpass type, and is also not spectrally neutral.

14. The system of claim 13 wherein the spectral response function of at least one of the expressed filter states is one of a monotonically increasing and a monotonically decreasing function of wavelength over the spectral range in which the probes emit.

15. The system of claim 13 wherein the spectral response function of at least one of the expressed filter states is one of a monotonically increasing function of wavelength, a monotonically decreasing function of wavelength, and a periodic function of wavelength over the spectral range in which the probes emit.

16. The system of claim 13 wherein at least one expressed filter state has significant transmission across the entire spectral range in which the probes emit.

17. The system of claim 16 wherein at least one expressed filter state is substantially neutral in its spectral response function across the entire spectral range in which the probes emit.

18. The system of claim 12 wherein the filter means comprises a liquid crystal tunable filter element with continuously tunable filter response.

19. The system of claim 12 wherein the filter means comprises a switchable liquid crystal filter element that selects between discrete spectral response functions and is not continuously tunable.

20. The system of claim 13 wherein the filter means comprises one of a liquid crystal interferometer and a mechanically-scanned interferometer, which produces a uniform optical path delay across the entire image.

21. The system of claim 20 wherein the filter means comprises a liquid crystal interferometer.

22. An imaging system for detecting and discriminating different light emissive probes contained within a sample, the probes being capable of emitting at different wavelengths over a spectral range, said system comprising optics that receive light emitted by the probes and form an image of the sample, a pixelated photodetector that receives light comprising the image of the sample, filter means for selectively filtering the light received by the detector according to two or more different filter states, each filter state having a predetermined spectral response function, electronic means that records photodetector readings for each pixel while the filter means expresses different filter states from among the predetermined spectral response functions, and calculation means for determining which probes are present at each point in the sample from the photodetector readings by comparing two or more of the photodetector readings obtained at different filter states, wherein one of the predetermined spectral filter states is a clear-state which transmits light of all probes with substantially neutral spectral response.

23. The system of claim 22 wherein the filter means comprises a liquid crystal tunable element with continuously variable response.

24. The system of claim 22 wherein the filter means comprises a switchable liquid crystal filter element that selects between discrete spectral response functions and is not continuously tunable.

25. The system of claim 22 wherein determination of probes at each pixel is made by the ratio of photodetector readings in filter states other than the clear-state relative to the reading in the clear state.

26. The system of claim 22 wherein the filter means is a liquid crystal filter with variable retardance between parallel or perpendicular polarizers.

27. The system of claim 22 wherein the filter means comprises in optical series a polarizer, at least a first retarder, a liquid crystal cell, at least a second retarder, and a second polarizer.

28. An imaging system for detecting and discriminating N different light emissive probes contained at a plurality of locations within a sample, the probes being capable of emitting at different wavelengths, said system comprising collection optics that receive light emitted by the probes filter means for selectively filtering the light received by the photodetector according to two or more different filter states, each filter state having a predetermined spectral response function, beamsplitting optics that spatially separate an image of the sample into at least two images that lie in distinct spectral bands from each other, at least two pixelated photodetectors that separately receive each of the spectrally distinct images, electronic means that records photodetector readings for each photodetector in time-sequence while the filter means expresses M filter states from among the predetermined spectral response functions, calculation means for determining which probes are present at each point in the sample by comparing the photodetector readings for a single photodetector obtained at two or more filter states, wherein the number of probes N which can be determined from a single photodetector exceeds the number of expressed filter states M, and wherein the transmission band of at least one filter state is not bandpass nor multiband pass in shape.

29. The system of claim 28 wherein the beamsplitting optics comprises a prism for separating the light emitted by the probes into at least the three primary colors of red, green and blue.

30. The system of claim 28 wherein the filter means is placed between the sample region and the beamsplitting optics.

31. The system of claim 28 wherein the filter means is placed between the collection optics and the beamsplitting optics.

32. The system of claim 28 wherein the filter means comprises a liquid crystal device.

33. The system of claim 28 wherein the filter means comprises at least one liquid crystal stage comprising a polarizer, at least a first retarder, a liquid crystal cell, and at least a second retarder in optical series.

34. The system of claim 33 wherein the filter means comprises at least two liquid crystal filter stages in optical series.

35. The system of claim 28 wherein at least three different emissive probes are capable of emitting light that is substantially within a single spectral band of the beamsplitting optics.

36. The system of claim 28 wherein at least eight different emissive probes are capable of emitting light that is substantially within a single spectral band of the beamsplitting optics.

37. A method for detecting and discriminating different light emissive probes contained at a plurality of locations within a sample comprising using optics to receive light emitted by N different emissive probes contained in a sample and to form an image of the sample, selectively filtering the image using filter means according to two or more different filter states, each filter state having a predetermined spectral response function, using a pixelated photodetector to receive the filtered image, recording photodetector readings in time-sequence while the filter means expresses M filter states from among the predetermined spectral response functions, and determining which probes are present at each point in the sample from the photodetector readings by comparing the intensities of the light emitted by each probe between two or more filter states, wherein the number of probes N which can be determined exceeds the number of expressed filter states M.

38. A method for detecting and discriminating different light emissive probes contained within a sample comprising using optics to receive light emitted by different emissive probes contained in a sample and to form an image of the sample, selectively filtering the image using filter means according to two or more different filter states, each filter state having a predetermined spectral response function, using a pixelated photodetector to receive the filtered image, recording photodetector readings in time-sequence while the filter means expresses different filter states from among the predetermined spectral response functions, and determining which probes are present at each point in the sample from the photodetector readings by comparing the intensities of the light emitted by each probe between two or more filter states, wherein at least one of the expressed filter states has a spectral response function that is not bandpass nor shortpass nor longpass type.

39. A method for detecting and discriminating different light emissive probes contained within a sample comprising using collection optics to receive light emitted by different emissive probes contained in a sample and forming an image of the sample, selectively filtering the image using filter means according to two or more different filter states, each filter state having a predetermined spectral response function, using a pixelated photodetector to receive the filtered image, recording photodetector readings for each pixel while the filter means expresses different filter states from among the predetermined spectral response functions, and determining which probes are present at each point in the sample from the photodetector readings by comparing the intensities of the light emitted by each probe between two or more filter states, wherein one of the predetermined spectral filter states is a clear-state which transmits light of all probes with substantially neutral spectral response.

40. A method for detecting and discriminating different light emissive probes contained at a plurality of locations within a sample comprising using collection optics to receive light emitted by N different emissive probes contained in a sample and forming an image of the sample, using filter means for selectively filtering the light received by the photodetector according to two or more different filter states, each filter state having a predetermined spectral response function, spatially separating the image of the sample by use of beamsplitting optics into at least two images that lie in distinct spectral bands from each other, separately receiving each of the spectrally distinct images with at least two pixelated photodetectors, recording photodetector readings for each photodetector in time-sequence while the filter means expresses M filter states from among the predetermined spectral response functions, and determining which probes are present at each point in the sample by comparing the photodetector readings for a single photodetector obtained at two or more filter states, wherein the number of probes N which can be determined from a single photodetector exceeds the number of expressed filter states M, and wherein the transmission band of at least one filter state is not bandpass nor multiband pass in shape.

\* \* \* \* \*